US008580831B2

(12) United States Patent
Bur et al.

(10) Patent No.: US 8,580,831 B2
(45) Date of Patent: Nov. 12, 2013

(54) FLUORINATED AMINOTRIAZOLE DERIVATIVES

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 67 days.

(21) Appl. No.: 13/376,966

(22) PCT Filed: Jun. 7, 2010

(86) PCT No.: PCT/IB2010/052509
§ 371 (c)(1),
(2), (4) Date: Dec. 8, 2011

(87) PCT Pub. No.: WO2010/143116
PCT Pub. Date: Dec. 16, 2010

(65) Prior Publication Data
US 2012/0101138 A1 Apr. 26, 2012

(30) Foreign Application Priority Data
Jun. 9, 2009 (WO) .................. PCT/IB2009/052445

(51) Int. Cl.
| A61K 31/422 | (2006.01) |
| A61K 31/427 | (2006.01) |
| C07D 413/14 | (2006.01) |
| C07D 417/14 | (2006.01) |

(52) U.S. Cl.
USPC ............................ 514/365; 514/374; 548/204

(58) Field of Classification Search
None
See application file for complete search history.

(56) References Cited

U.S. PATENT DOCUMENTS

| 2004/0043904 A1 | 3/2004 | Yamaguchi et al. |
| 2010/0331378 A1 | 12/2010 | Bur et al. |
| 2011/0034516 A1 | 2/2011 | Bur et al. |
| 2012/0115841 A1 | 5/2012 | Bur et al. |
| 2012/0115916 A1 | 5/2012 | Bur et al. |

FOREIGN PATENT DOCUMENTS

| JP | 62-234018 | 10/1987 |
| WO | WO 03/082314 | 10/2003 |
| WO | WO 2005/047899 | 5/2005 |
| WO | WO 2007/055941 | 5/2007 |
| WO | WO 2009/025793 | 2/2009 |
| WO | WO 2009/077954 | 6/2009 |
| WO | WO 2009/077990 | 6/2009 |
| WO | WO 2010/134014 | 11/2010 |
| WO | WO 2010/143158 | 12/2010 |

OTHER PUBLICATIONS

Burli, R. W. et al.; "Potent hFPRL1 (ALXR) agonists as potential anti-inflammatory agents;" Bioorganic & Medicinal Chemistry Letters, Pergamon, Elsevier Science, GB LNKD-DOI: 10.1016/J.BMCL; vol. 16, No. 15, pp. 3713-3718; XP025106261; ISSN: 0960-894X; Jul. 15, 2006.

Chiang, Nan et al.; "The Lipoxing Receptor ALX: Potent Ligand-Specific and Stereoselective Actions in Vivo"; Pharmacological Reviews, vol. 58, No. 3, pp. 463-487; 2006.

Eagles, T.E. et al.; "Some Nitro-1,2,3-Triazoles"; Organic Preparations and Procedures, 2(2), pp. 117-119; 1970.

Evans, David et al.; "Drug-Protein Adducts: An Industry Perspective on Minimizing the Potential for Drug Bioactivation in Drug Discovery and Development"; Chem. Res. Toxicol, vol. 17, pp. 3-16; 2004.

Gould, Philip L.; "Salt selection for basic drugs"; International Journal of Pharmaceutics, vol. 33, pp. 201-217; 1986.

Greene, Theodora W. et al.; "Protective Groups in Organic Synthesis"; Wiley-Interscience Publication; Third Edition; 1999; ISBN 0-471-22057-4.

Le, Yingying et al.; "Biologically Active Peptides Interacting with the G Protein-Coupled Formylpeptide Receptors"; Protein & Peptide Letters, vol. 14, pp. 846-853; 2007.

Neuman, Peter N., "Nitro Derivatives of Phenyl-1,2,3-triazole (1)"; J. Heterocycl. Chem., 8, 51-56, 1971.

Remington; "Pharmaceutical Manufacturing"; The Science and Practice of Pharmacy, 21$^{st}$ Edition, Part 5; published by Lippincott Williams & Wilkins; 2005.

Schwab, Jan M. et al; "Lipoxins and new lipid mediators in the resolution of inflammation"; Current Opinion in Pharmacology, vol. 6, pp. 414-420; 2006.

Yazawa, Hiroshi et al.; "β Amyloid peptide ($A\beta_{42}$) is internalized via the G-Protein-Coupled receptor FPRL1 and forms fibrillar aggregates in macrophages[1]"; FASEB Journal, vol. 15, pp. 2454-2462; Nov. 2001.

Ying, Guoguang et al.; "Humanin, a Newly Identified Neuroprotective Factor, Uses the G Protein-Coupled Formylpeptide Receptor-Like-1 as a Functional Receptor"; Journal of Immunology, Vo. 172, pp. 7078-7085; 2004.

(Continued)

Primary Examiner — Kamal Saeed

(74) Attorney, Agent, or Firm — Hunton & Williams LLP

(57) ABSTRACT

The invention relates to fluorinated aminotriazole derivatives of formula (I), wherein A, $R^1$ and $R^2$ are as defined in the description, their preparation and their use as pharmaceutically active compounds.

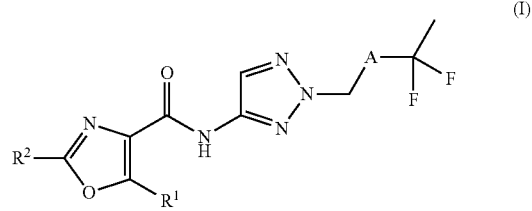

22 Claims, No Drawings

(56) References Cited

OTHER PUBLICATIONS

Mallamo et al., "Antiandrogenic Steroidal Sulfonyl Heterocyles. Utility of Electrostatic Complementarity in Defining Bioisosteric Sulfonyl Heterocycles"; Journal of Medicinal Chemistry, vol. 35, No. 10, 1992, pp. 1663-1670.

Obushak, N. D. et al.; "Heterocyclic syntheses on the basis of arylation products of unsaturated compounds: X.*3-Aryl-2-chloropropanals as reagents for the synthesis of 2-amino-1,3-thiazole derivatives;" Russian Journal of Organic Chemistry, Consultants Bureau, US LNKD-DOI: 10.123/B:RUJO.0000034976.75646.85, vol. 40, No. 3, pp. 383-389; XP009097222; ISSN: 1070-4280; Jan. 1, 2004.

Wermuth, C. G.; "Molecular variations based on isosteric replacements"; Practice of Medicinal Chemistry, pp. 203-237; XP002190259; Jan. 1, 1996.

United States Patent and Trademark Office—Non Final Office Action Mailed Mar. 12, 2012 for U.S. Appl. No. 12/809,545, "Aminotriazole Derivatives As Alx Agonists," 18 pages.

FLUORINATED AMINOTRIAZOLE DERIVATIVES

CROSS-REFERENCE TO RELATED APPLICATIONS

This application is the national phase application of PCT/IB2010/052509, filed Jun. 7, 2010, which claims the benefit of PCT/IB2009/052445, filed Jun. 9, 2009, the contents of each of which are hereby incorporated by reference in their entirety.

FIELD OF THE INVENTION

The present invention relates to fluorinated aminotriazole derivatives of formula (I) and their use as pharmaceuticals. The invention also concerns related aspects including processes for the preparation of the compounds, pharmaceutical compositions containing one or more compounds of formula (I), and especially their use as ALX receptor agonists.

BACKGROUND OF THE INVENTION

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogs, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

BRIEF SUMMARY OF THE INVENTION

The present invention provides fluorinated aminotriazole derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Compared to aminotriazole derivatives disclosed in WO 2009/077990, which are also ALX receptor agonists, compounds of the present application demonstrated a significantly improved profile when tested in a covalent binding assay, which is expected to correlate to an improved safety profile (Evans et al. Chem. Res. Toxicol., 2004, 17, 3-16).

DETAILED DESCRIPTION OF PREFERRED EMBODIMENTS

Various embodiments of the invention are presented hereafter:

1) The present invention relates to fluorinated aminotriazole derivatives of formula (I),

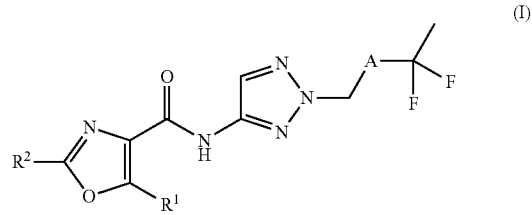

wherein
A represents a heteroaryl-group, wherein the two attachment-points of said heteroaryl-group are in a 1,3-arrangement;
$R^1$ represents phenyl which is unsubstituted, mono- or di-substituted (notably unsubstituted or mono-substituted), wherein the substituents are independently selected from the group consisting of halogen, methyl, methoxy, trifluoromethyl, trifluoromethoxy and dimethylamino; and
$R^2$ represents hydrogen, methyl, ethyl or cyclopropyl (notably hydrogen or methyl);
and to the salts (in particular pharmaceutically acceptable salts) of such compounds.

The following paragraphs provide definitions of the various chemical moieties for the compounds according to the invention and are intended to apply uniformly throughout the specification and claims unless an otherwise expressly set out definition provides a broader or narrower definition.

The term halogen means fluoro, chloro, bromo or iodo, preferably fluoro, chloro or bromo and most preferably fluoro or chloro.

The term "heteroaryl", used alone or in combination, means a 5-membered monocyclic aromatic ring containing 1, 2 or 3 (preferably 1 or 2) heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl and triazolyl. Preferred examples are furanyl (notably furan-2,5-diyl), oxazolyl (notably oxazol-2,4-diyl) and thiazolyl (notably thiazol-2,4-diyl). Most preferred examples are furan-2,5-diyl, oxazol-2,4-diyl with 1,1-difluoroethyl being attached to the 4-position and thiazol-2,4-diyl with 1,1-difluoroethyl being attached to the 4-position (and especially oxazol-2,4-diyl with 1,1-difluoroethyl being attached to the 4-position). A further most preferred example is oxazol-2,4-diyl with 1,1-difluoroethyl being attached to the 2-position.

The term "1,3-arrangement" as used in the specification of "A" means that the two atoms of the heteroaryl-group which are attached to the triazole-methyl moiety and to the 1,1-difluoroethyl moiety are separated from each other by one atom; for example, if "A" represents furan-2,5-diyl the arrangement of the substituents is as shown in the figure below

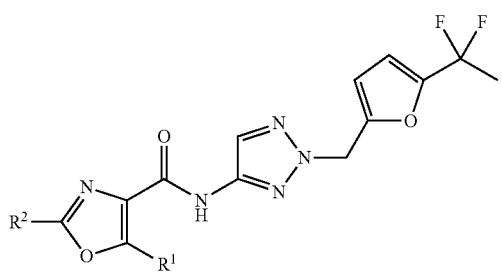

2) A further embodiment of the invention relates to fluorinated aminotriazole derivatives according to embodiment 1), wherein A represents a group selected from furanyl (notably furan-2,5-diyl), oxazolyl (notably oxazol-2,4-diyl) and thiazolyl (notably thiazol-2,4-diyl), wherein the two attachment-points of said group are in a 1,3-arrangement;

$R^1$ represents phenyl which is unsubstituted, mono- or di-substituted (notably unsubstituted or mono-substituted), wherein the substituents are independently selected from the group consisting of fluoro, chloro, methyl, methoxy, trifluoromethyl, trifluoromethoxy and dimethylamino; and $R^2$ represents hydrogen, methyl or ethyl (notably hydrogen or methyl);

and to the salts (in particular pharmaceutically acceptable salts) of such compounds.

3) A further embodiment of the invention relates to fluorinated aminotriazole derivatives according to any one of embodiments 1) or 2), wherein A represents furan-2,5-diyl (with 1,1-difluoroethyl preferably being attached to the 5-position), oxazol-2,4-diyl (with 1,1-difluoroethyl preferably being attached to the 4-position) or thiazol-2,4-diyl (with 1,1-difluoroethyl preferably being attached to the 4-position);

$R^1$ represents phenyl which is unsubstituted or mono-substituted, wherein the substituent is selected from the group consisting of fluoro, chloro, methyl, methoxy, trifluoromethyl, trifluoromethoxy and dimethylamino; and $R^2$ represents hydrogen or methyl;

and to the salts (in particular pharmaceutically acceptable salts) of such compounds.

4) A further embodiment of the invention relates to fluorinated aminotriazole derivatives according to any one of embodiments 1) or 2), wherein A represents a group selected from furanyl (notably furan-2,5-diyl), oxazolyl (notably oxazol-2,4-diyl) and thiazolyl (notably thiazol-2,4-diyl), wherein the two attachment-points of said group are in a 1,3-arrangement;

and to the salts (in particular pharmaceutically acceptable salts) of such compounds.

5) A further embodiment of the invention relates to fluorinated aminotriazole derivatives according to any one of embodiments 1) to 4), wherein A represents furan-2,5-diyl (with 1,1-difluoroethyl preferably being attached to the 5-position), oxazol-2,4-diyl (with 1,1-difluoroethyl preferably being attached to the 4-position) or thiazol-2,4-diyl (with 1,1-difluoroethyl preferably being attached to the 4-position);

and to the salts (in particular pharmaceutically acceptable salts) of such compounds.

6) A further embodiment of the invention relates to fluorinated aminotriazole derivatives according to any one of embodiments 1) to 4), wherein A represents a furanyl-group (notably furan-2,5-diyl), wherein the two attachment-points of said group are in a 1,3-arrangement;

and to the salts (in particular pharmaceutically acceptable salts) of such compounds.

7) A further embodiment of the invention relates to fluorinated aminotriazole derivatives according to any one of embodiments 1) to 5), wherein A represents furan-2,5-diyl;

and to the salts (in particular pharmaceutically acceptable salts) of such compounds.

8) A further embodiment of the invention relates to fluorinated aminotriazole derivatives according to any one of embodiments 1) to 4), wherein A represents an oxazolyl-group (notably oxazol-2,4-diyl), wherein the two attachment-points of said group are in a 1,3-arrangement;

and to the salts (in particular pharmaceutically acceptable salts) of such compounds.

9) A further embodiment of the invention relates to fluorinated aminotriazole derivatives according to any one of embodiments 1) to 5), wherein A represents oxazol-2,4-diyl (with 1,1-difluoroethyl preferably being attached to the 4-position);

and to the salts (in particular pharmaceutically acceptable salts) of such compounds.

10) A further embodiment of the invention relates to fluorinated aminotriazole derivatives according to any one of embodiments 1) to 4), wherein A represents a thiazolyl-group (notably thiazol-2,4-diyl), wherein the two attachment-points of said group are in a 1,3-arrangement;

and to the salts (in particular pharmaceutically acceptable salts) of such compounds.

11) A further embodiment of the invention relates to fluorinated aminotriazole derivatives according to any one of embodiments 1) to 5), wherein A represents thiazol-2,4-diyl (with 1,1-difluoroethyl preferably being attached to the 4-position);
and to the salts (in particular pharmaceutically acceptable salts) of such compounds.

12) A further embodiment of the invention relates to fluorinated aminotriazole derivatives according to any one of embodiments 1) to 11), wherein
$R^1$ represents phenyl which is unsubstituted, mono- or di-substituted (notably unsubstituted or mono-substituted), wherein the substituents are independently selected from the group consisting of fluoro, chloro, methyl, methoxy, trifluoromethyl, trifluoromethoxy and dimethylamino;
and to the salts (in particular pharmaceutically acceptable salts) of such compounds.

13) A further embodiment of the invention relates to fluorinated aminotriazole derivatives according to any one of embodiments 1) to 11), wherein
$R^1$ represents unsubstituted phenyl;
and to the salts (in particular pharmaceutically acceptable salts) of such compounds.

14) A further embodiment of the invention relates to fluorinated aminotriazole derivatives according to any one of embodiments 1) to 11), wherein
$R^1$ represents phenyl which is mono- or di-substituted (notably mono-substituted), wherein the substituents are independently selected from the group consisting of halogen, methyl, methoxy, trifluoromethyl, trifluoromethoxy and dimethylamino;
and to the salts (in particular pharmaceutically acceptable salts) of such compounds.

15) A further embodiment of the invention relates to fluorinated aminotriazole derivatives according to any one of embodiments 1) to 11), wherein
$R^1$ represents phenyl, which is mono-substituted with fluoro, chloro, methyl or trifluoromethyl (and notably phenyl, which is mono-substituted in 3-position with fluoro, chloro, methyl or trifluoromethyl);
and to the salts (in particular pharmaceutically acceptable salts) of such compounds.

16) A further embodiment of the invention relates to fluorinated aminotriazole derivatives according to any one of embodiments 1) to 11), wherein
$R^1$ represents phenyl, which is mono-substituted with fluoro or chloro (and notably 3-fluoro-phenyl or 3-chloro-phenyl);
and to the salts (in particular pharmaceutically acceptable salts) of such compounds.

17) A further embodiment of the invention relates to fluorinated aminotriazole derivatives according to any one of embodiments 1) to 11), wherein
$R^1$ represents phenyl, which is mono-substituted with methyl (and notably 3-methyl-phenyl);
and to the salts (in particular pharmaceutically acceptable salts) of such compounds.

18) A further embodiment of the invention relates to fluorinated aminotriazole derivatives according to any one of embodiments 1) to 11), wherein
$R^1$ represents phenyl, which is mono-substituted with methoxy (and notably 3-methoxy-phenyl);
and to the salts (in particular pharmaceutically acceptable salts) of such compounds.

19) A further embodiment of the invention relates to fluorinated aminotriazole derivatives according to any one of embodiments 1) to 11), wherein
$R^1$ represents phenyl, which is mono-substituted with trifluoromethyl (and notably 3-trifluormethyl-phenyl);
and to the salts (in particular pharmaceutically acceptable salts) of such compounds.

20) A further embodiment of the invention relates to fluorinated aminotriazole derivatives according to any one of embodiments 1) to 11), wherein
$R^1$ represents phenyl, which is mono-substituted with trifluoromethoxy (and notably 3-trifluoromethoxy-phenyl);
and to the salts (in particular pharmaceutically acceptable salts) of such compounds.

21) A further embodiment of the invention relates to fluorinated aminotriazole derivatives according to any one of embodiments 1) to 11), wherein
$R^1$ represents phenyl, which is mono-substituted with dimethylamino (and notably 3-dimethylamino-phenyl);
and to the salts (in particular pharmaceutically acceptable salts) of such compounds.

22) A further embodiment of the invention relates to fluorinated aminotriazole derivatives according to any one of embodiments 1), 2) or 4) to 21), wherein
$R^2$ represents hydrogen, methyl or ethyl;
and to the salts (in particular pharmaceutically acceptable salts) of such compounds.

23) A further embodiment of the invention relates to fluorinated aminotriazole derivatives according to any one of embodiments 1) to 21), wherein
$R^2$ represents hydrogen or methyl;
and to the salts (in particular pharmaceutically acceptable salts) of such compounds.

24) A further embodiment of the invention relates to fluorinated aminotriazole derivatives according to any one of embodiments 1) to 21), wherein
$R^2$ represents hydrogen; and to the salts (in particular pharmaceutically acceptable salts) of such compounds.

25) A further embodiment of the invention relates to fluorinated aminotriazole derivatives according to any one of embodiments 1) to 21), wherein
$R^2$ represents methyl or ethyl (notably methyl);
and to the salts (in particular pharmaceutically acceptable salts) of such compounds.

26) A further embodiment of the invention relates to fluorinated aminotriazole derivatives according to embodiment 1), wherein
A represents oxazol-2,4-diyl (with 1,1-difluoroethyl preferably being attached to the 4-position);
$R^1$ represents phenyl which is unsubstituted, mono- or di-substituted, wherein the substituents are independently selected from the group consisting of fluoro, methyl and dimethylamino; and
$R^2$ represents hydrogen or methyl;
and to the salts (in particular pharmaceutically acceptable salts) of such compounds.

27) A further embodiment of the invention relates to fluorinated aminotriazole derivatives according to any one of embodiments 1) to 5), 8) or 12) to 26), wherein
A represents oxazol-2,4-diyl with 1,1-difluoroethyl being attached to the 2-position;
and to the salts (in particular pharmaceutically acceptable salts) of such compounds.

28) A further embodiment of the invention relates to fluorinated aminotriazole derivatives according to any one of embodiments 1), 2), 4) to 12), 14) or 22) to 27), wherein
$R^1$ represents 3-dimethylamino-4-fluoro-phenyl;
and to the salts (in particular pharmaceutically acceptable salts) of such compounds.

29) Preferred compounds of formula (I) as defined in embodiment 1) are selected from the group consisting of:

2-Methyl-5-m-tolyl-oxazole-4-carboxylic acid{2-[5-(1,1-difluoro-ethyl)-furan-2-ylmethyl]-2H-[1,2,3]triazol-4-yl}-amid;

5-Phenyl-oxazole-4-carboxylic acid{2-[4-(1,1-difluoro-ethyl)-thiazol-2-ylmethyl]-2H-[1,2,3]triazol-4-yl}-amide;

2-Methyl-5-m-tolyl-oxazole-4-carboxylic acid{2-[4-(1,1-difluoro-ethyl)-thiazol-2-ylmethyl]-2H-[1,2,3]triazol-4-yl}-amide;

2-Methyl-5-phenyl-oxazole-4-carboxylic acid{2-[5-(1,1-difluoro-ethyl)-furan-2-ylmethyl]-2H-[1,2,3]triazol-4-yl}-amide;

5-(3,5-Difluoro-phenyl)-2-methyl-oxazole-4-carboxylic acid{2-[4-(1,1-difluoro-ethyl)-thiazol-2-ylmethyl]-2H-[1,2,3]triazol-4-yl}-amide;

2-Methyl-5-(3-trifluoromethyl-phenyl)-oxazole-4-carboxylic acid{2-[4-(1,1-difluoro-ethyl)-thiazol-2-ylmethyl]-2H-[1,2,3]triazol-4-yl}-amide;

5-(3-Chloro-phenyl)-oxazole-4-carboxylic acid{2-[5-(1,1-difluoro-ethyl)-furan-2-ylmethyl]-2H-[1,2,3]triazol-4-yl}-amide;

5-(3-Methoxy-phenyl)-oxazole-4-carboxylic acid{2-[4-(1,1-difluoro-ethyl)-thiazol-2-ylmethyl]-2H-[1,2,3]triazol-4-yl}-amide;

2-Cyclopropyl-5-phenyl-oxazole-4-carboxylic acid{2-[4-(1,1-difluoro-ethyl)-thiazol-2-ylmethyl]-2H-[1,2,3]triazol-4-yl}-amide;

2-Methyl-5-phenyl-oxazole-4-carboxylic acid{2-[4-(1,1-difluoro-ethyl)-thiazol-2-ylmethyl]-2H-[1,2,3]triazol-4-yl}-amide;

5-(3-Fluoro-phenyl)-oxazole-4-carboxylic acid{2-[5-(1,1-difluoro-ethyl)-furan-2-ylmethyl]-2H-[1,2,3]triazol-4-yl}-amide;

5-(3-Chloro-phenyl)-oxazole-4-carboxylic acid{2-[4-(1,1-difluoro-ethyl)-thiazol-2-ylmethyl]-2H-[1,2,3]triazol-4-yl}-amide;

5-(3-Fluoro-5-methyl-phenyl)-2-methyl-oxazole-4-carboxylic acid{2-[4-(1,1-difluoro-ethyl)-thiazol-2-ylmethyl]-2H-[1,2,3]triazol-4-yl}-amide;

2-Methyl-5-(3-trifluoromethoxy-phenyl)-oxazole-4-carboxylic acid{2-[4-(1,1-difluoro-ethyl)-thiazol-2-ylmethyl]-2H-[1,2,3]triazol-4-yl}-amide;

5-(3-Chloro-phenyl)-2-methyl-oxazole-4-carboxylic acid{2-[5-(1,1-difluoro-ethyl)-furan-2-ylmethyl]-2H-[1,2,3]triazol-4-yl}-amide;

5-(4-Fluoro-phenyl)-oxazole-4-carboxylic acid{2-[5-(1,1-difluoro-ethyl)-furan-2-ylmethyl]-2H-[1,2,3]triazol-4-yl}-amide;

5-m-Tolyl-oxazole-4-carboxylic acid{2-[4-(1,1-difluoro-ethyl)-thiazol-2-ylmethyl]-2H-[1,2,3]triazol-4-yl}-amide;

5-(3,5-Difluoro-phenyl)-2-methyl-oxazole-4-carboxylic acid{2-[5-(1,1-difluoro-ethyl)-furan-2-ylmethyl]-2H-[1,2,3]triazol-4-yl}-amide;

5-(3-Dimethylamino-phenyl)-oxazole-4-carboxylic acid{2-[5-(1,1-difluoro-ethyl)-furan-2-ylmethyl]-2H-[1,2,3]triazol-4-yl}-amide;

5-(3-Fluoro-phenyl)-oxazole-4-carboxylic acid{2-[4-(1,1-difluoro-ethyl)-thiazol-2-ylmethyl]-2H-[1,2,3]triazol-4-yl}-amide;

5-(3-Methoxy-phenyl)-oxazole-4-carboxylic acid{2-[5-(1,1-difluoro-ethyl)-furan-2-ylmethyl]-2H-[1,2,3]triazol-4-yl}-amide;

5-(3-Dimethylamino-phenyl)-oxazole-4-carboxylic acid{2-[4-(1,1-difluoro-ethyl)-thiazol-2-ylmethyl]-2H-[1,2,3]triazol-4-yl}-amide;

5-m-Tolyl-oxazole-4-carboxylic acid{2-[5-(1,1-difluoro-ethyl)-furan-2-ylmethyl]-2H-[1,2,3]triazol-4-yl}-amide;

2-Methyl-5-(3-trifluoromethyl-phenyl)-oxazole-4-carboxylic acid{2-[5-(1,1-difluoro-ethyl)-furan-2-ylmethyl]-2H-[1,2,3]triazol-4-yl}-amide;

5-(4-Fluoro-phenyl)-oxazole-4-carboxylic acid{2-[4-(1,1-difluoro-ethyl)-thiazol-2-ylmethyl]-2H-[1,2,3]triazol-4-yl}-amide;

5-(3-Fluoro-5-methyl-phenyl)-2-methyl-oxazole-4-carboxylic acid{2-[5-(1,1-difluoro-ethyl)-furan-2-ylmethyl]-2H-[1,2,3]triazol-4-yl}-amide;

2-Methyl-5-(3-trifluoromethoxy-phenyl)-oxazole-4-carboxylic acid{2-[5-(1,1-difluoro-ethyl)-furan-2-ylmethyl]-2H-[1,2,3]triazol-4-yl}-amide;

5-Phenyl-oxazole-4-carboxylic acid{2-[5-(1,1-difluoro-ethyl)-furan-2-ylmethyl]-2H-[1,2,3]triazol-4-yl}-amide;

5-(3-Chloro-phenyl)-2-methyl-oxazole-4-carboxylic acid{2-[4-(1,1-difluoro-ethyl)-thiazol-2-ylmethyl]-2H-[1,2,3]triazol-4-yl}-amide;

2-Ethyl-5-phenyl-oxazole-4-carboxylic acid{2-[4-(1,1-difluoro-ethyl)-thiazol-2-ylmethyl]-2H-[1,2,3]triazol-4-yl}-amide; and 2-Methyl-5-m-tolyl-oxazole-4-carboxylic acid{2-[4-(1,1-difluoro-ethyl)-oxazol-2-ylmethyl]-2H-[1,2,3]triazol-4-yl}-amide; or salts (in particular pharmaceutically acceptable salts) of such compounds.

30) Further preferred compounds of formula (I) as defined in embodiment 1) are selected from the group consisting of:

N-(2-((2-(1,1-Difluoroethyl)oxazol-4-yl)methyl)-2H-1,2,3-triazol-4-yl)-2-methyl-5-(m-tolyl)oxazole-4-carboxamide;

2-Methyl-5-phenyl-oxazole-4-carboxylic acid{2-[4-(1,1-difluoro-ethyl)-oxazol-2-ylmethyl]-2H-[1,2,3]triazol-4-yl}-amide;

5-(3-Dimethylamino-phenyl)-oxazole-4-carboxylic acid{2-[4-(1,1-difluoro-ethyl)-oxazol-2-ylmethyl]-2H-[1,2,3]triazol-4-yl}-amide;

5-(3-Dimethylamino-4-fluoro-phenyl)-oxazole-4-carboxylic acid{2-[4-(1,1-difluoro-ethyl)-oxazol-2-ylmethyl]-2H-[1,2,3]triazol-4-yl}-amide; and 5-(3-Dimethylamino-4-fluoro-phenyl)-2-methyl-oxazole-4-carboxylic acid{2-[4-(1,1-difluoro-ethyl)-oxazol-2-ylmethyl]-2H-[1,2,3]triazol-4-yl}-amide;

or salts (in particular pharmaceutically acceptable salts) of such compounds.

31) A most preferred compound of formula (I) as defined in embodiment 1) is:

2-Methyl-5-m-tolyl-oxazole-4-carboxylic acid{2-[4-(1,1-difluoro-ethyl)-oxazol-2-ylmethyl]-2H-[1,2,3]triazol-4-yl}-amide;

or a salt (in particular pharmaceutically acceptable salt) thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 31), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 31), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.
2) Further inflammatory diseases, obstructive airway diseases and allergic conditions include bronchitis of whatever type or genesis.
3) Further inflammatory diseases, obstructive airway diseases and allergic conditions include bronchiectasis, and pneumoconiosis of whatever type or genesis.
4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.
5) In a further embodiment the compounds of formula (I) according to any one of embodiments 1) to 31), or pharmaceutically acceptable salts thereof, are particularly suitable for the prevention or treatment of inflammatory diseases. Inflammatory diseases include one, several or all of the following groups of diseases and disorders:
   5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.
   5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.
   5c) Further inflammatory diseases also relate to diseases or conditions having an inflammatory component. Diseases or conditions having an inflammatory component include, but are not limited to, diseases and conditions affecting the eye such as uveits (anterior, intermediate and posterior), Behcet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).
   5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 31), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 31), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4v, GUN-7 wt, AG204, AG206, AG208, HCM305, HCM308, HCM342, mSTD104, and HCM309.

Further, the compounds of formula (I) according to any one of embodiments 1) to 31), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 31), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid βdeposition of amyloid plaques.

Further, the compounds of formula (I) according to any one of embodiments 1) to 31), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 31), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 31), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Straussler-Scheinker syndrome (GSS), Fatal Familial Insomnia (FFI) and Creutzfeldt-Jakob Disease (CJD).

Further, the compounds of formula (I) according to any one of embodiments 1) to 31), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 31), or pharmaceutically acceptable salts thereof, are suitable for the modulation of immune responses. The modulation of immune responses includes, but is not limited to, methods based on the administration to a subject a composition of at least one antigen and at least one compound of formula (I) according to any one of embodiments 1) to 31), or pharmaceutically acceptable salts thereof. In some cases, the antigen-containing composition is administrated first, followed by administration of a composition of at least one compounds of formula (I) according to any one of embodiments 1) to 31), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 31), or pharmaceutically acceptable salts thereof, and the antigen, as compared to sole administration of the antigen;
2) A greater sensitivity to small amounts of antigen (e.g., toxin or pathogen) or antigens that do not habitually induce strong immune responses; and
3) More effective anti-tumor therapies.

Further, the compounds of formula (I) according to any one of embodiments 1) to 31), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 31), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection);
2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;
3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);
4) HIV-mediated retroviral infections such as diseases and disorders caused by HIV-1 and HIV-2 strains such as GUN-4v, GUN-7 wt, AG204, AG206, AG208, HCM305, HCM308, HCM342, mSTD104, and HCM309;
5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;
6) Neurological disorders such as stroke, cerebral ischemia, Alzheimer's disease, and Parkinson's disease;
7) Prion-mediated diseases, also known as transmissible spongiform encephalopathies (TSEs), such as kuru, Gerstmann-Strä ussler-Scheinker syndrome (GSS), Fatal Familial Insomnia (FFI) and Creutzfeldt-Jakob Disease (CJD);
8) Amyloid-mediated disorders;
9) Cystic fibrosis, wound healing and inflammatory diseases caused by pathogenic organisms.

The invention also relates to the use of a compound of formula (I) according to any one of embodiments 1) to 31) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 31).

A pharmaceutical composition according to the present invention contains at least one compound of formula (I) according to any one of embodiments 1) to 31) (or a pharmaceutically acceptable salt thereof) as the active agent and optionally carriers and/or diluents and/or adjuvants.

The compounds of formula (I) according to any one of embodiments 1) to 31) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 31), or a pharmaceutically acceptable salt thereof.

Any reference to a compound of formula (I) in this text is to be understood as referring also to the salts (and especially the pharmaceutically acceptable salts) of such compounds, as appropriate and expedient. The preferences indicated for the compounds of formula (I) of course apply mutatis mutandis to the salts and pharmaceutically acceptable salts of the compounds of formula (I). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups A, $R^1$ and $R^2$ are as defined for formula (I). Other abbreviations used are defined in the experimental section. Generic group $R^u$ as used in structure 6 below represents hydrogen or methyl. Generic groups $R^x$ as used in structure 4 below represent methyl or ethyl or both Rx together form an ethane-1,2-diyl bridge. The generic carboxyl protecting group R as used e.g. in structure 5, in the schemes below and in the general procedures of the experimental part represents methyl, ethyl, n-propyl, iso-propyl, n-butyl, iso-butyl, sec-butyl or tert-butyl and preferably methyl or ethyl. The generic group $Si^{PG}$ as used in structure 6 below represents an appropriate silyl protecting group such as TMS, TIPS, TBDMS or TBDPS, preferably TBDMS.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups A, $R^1$ and $R^2$ might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

A. Synthesis of final products

Section A) hereafter describes general methods for preparing compounds of formula (I).

A) The compounds of formula (I) can be prepared from amines of structure 1 by reaction with the appropriate carboxylic acid chloride at a temperature about rt in a suitable solvent such as $CH_2Cl_2$ in presence of a base such as $Et_3N$ or DIPEA. The appropriate carboxylic acid chloride can be prepared at a temperature about rt from the corresponding carboxylic acid of structure 7 by reaction with a reagent such as oxalyl chloride in presence of DMF in a suitable solvent such as toluene. Alternatively, amines of structure 1 can be coupled with the appropriate carboxylic acid of structure 7 using standard amide coupling conditions such as EDC/HOBt/DMAP, TBTU, HBTU or PyBOP in presence of a base such as DIPEA or $Et_3N$ at a temperature about rt in a suitable solvent such as $CH_2Cl_2$ to give compounds of formula (I).

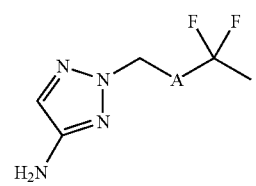

Structure 1

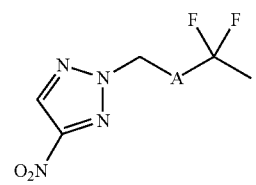

Structure 2

Compounds of structure 1 can be obtained from compounds of structure 2 by reduction of the nitro group either by hydrogenation in the presence of a metal catalyst such as Pd/C, Pt/C or $PtO_2$ at a temperature about rt in a suitable solvent such as MeOH or EtOH, or by reduction with a metal such as iron in a solvent mixture such as $H_2O$/EtOH in the presence of ammonium chloride at a temperature ranging from rt to 95° C.

B. Synthesis of Intermediates

Compounds of structure 2 may be prepared from compounds of structure 3 by fluorination with a fluorinating agent such as (diethylamino)sulphur trifluoride or (bis(2-methoxyethyl)amino)sulphur trifluoride in presence of a catalytic amount of an alcohol such as EtOH in a solvent such as toluene at a temperature about 60° C.

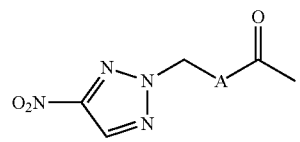

Structure 3

Alternatively, compounds of structure 2 may be prepared by reacting Ms-O—$CH_2$-A-$CF_2$—$CH_3$ or Cl—$CH_2$-A-$CF_2$—$CH_3$ with 4-nitro-2H-[1,2,3]triazole (T. E. Eagles et al. Organic preparations and procedures 2 (2), 117-119, 1970; P. N. Neuman J. Heterocycl. Chem. 8, 51-56, 1971) in the presence of a base such as $K_2CO_3$ or $Cs_2CO_3$ in a solvent such as acetone or AcCN at a temperature about rt or 80° C. (with or without addition of tetrabutylammonium bromide) using in case A represents oxazole-2,4-diyl an oxazole derivative such as (2-(1,1-difluoroethyl)oxazol-4-yl)methyl methanesulfonate, or another appropriate reagent of formula Ms-O—$CH_2$-A-$CF_2$—$CH_3$ or Cl—$CH_2$-A-$CF_2$—$CH_3$. Alternatively, the reaction may be performed in the presence of a base such as DIPEA in a solvent such as DMF, acetone or a mixture of both at a temperature about rt or 50° C.

Compounds of structure 3 may be prepared by reacting Ms-O—$CH_2$-A-C(O)—$CH_3$ or Cl—$CH_2$-A-C(O)—$CH_3$ with 4-nitro-2H-[1,2,3]triazole (T. E. Eagles et al. Organic preparations and procedures 2 (2), 117-119, 1970; P. N. Neuman J. Heterocycl. Chem. 8, 51-56, 1971) in the presence of a base such as $K_2CO_3$ or $Cs_2CO_3$ in a solvent such as acetone or AcCN at a temperature about rt or 80° C. (with or without addition of tetrabutylammonium bromide) using in case A represents furan-2,5-diyl a furan derivative such as 1-(5-chloromethyl-furan-2-yl)-ethanone or in case A represents oxazole-2,4-diyl an oxazole derivative such as methanesulfonic acid 4-acetyl-oxazol-2-ylmethyl ester or in case A represents isoxazole-2,4-diyl an isoxazole derivative such as 1-(5-chloromethyl-isoxazol-3-yl)-ethanone, or another appropriate reagent of formula Ms-O—CH$_2$-A-C(O)—CH$_3$ or Cl—CH$_2$-A-C(O)—CH$_3$. Alternatively, the reaction may be performed in the presence of a base such as DIPEA in a solvent such as DMF, acetone or a mixture of both at a temperature about rt or 50° C.

Alternatively, compounds of structure 3 can be prepared by deprotecting a ketal of structure 4 using standard conditions like:
- using an acid such as diluted aqueous HCl in a solvent such as THF at a temperature about rt; or
- using SCX silica gel in a solvent such as MeOH; or
- using a silica gel bound acid such as tosic acid in a solvent such as MeOH; or
- using an acid such as formic acid in a solvent such as water at a temperature ranging from about 0° C. to about 50° C.

Structure 4

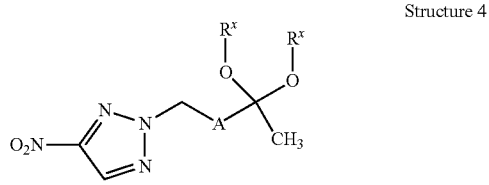

Alternatively, compounds of structure 3 can be prepared starting from the respective compounds of structure 5 by the following sequence:
- Reduction of an ester of structure 5 to the corresponding alcohol under standard reducing conditions using a reagent such as NaBH$_4$ in a solvent such as MeOH at a temperature about rt or, alternatively, a reagent such as DiBAL in a solvent such as THF at a temperature ranging from about −78° C. to rt;
- Oxidation of the alcohol to the corresponding aldehyde under standard oxidative conditions using reagents such as MnO$_2$, pyridinium chlorochromate or NMO/TPAP in a solvent such as AcCN or CH$_2$Cl$_2$ at a temperature about rt;
- Addition of an alkyl Grignard reagent at a temperature below rt (preferably about −78° C.) in a solvent such as THF, or, alternatively, addition of a trialkylaluminum reagent at a temperature about 0° C. in a solvent such as CH$_2$Cl$_2$ providing the corresponding secondary alcohol; and
- Oxidation of the alcohol under standard oxidative conditions using reagents such as TPAP/NMO or MnO$_2$ in a solvent such as CH$_2$Cl$_2$ or AcCN at a temperature about rt to provide the compound of structure 3.

Structure 5

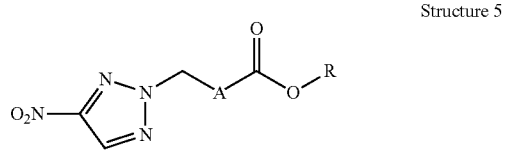

Alternatively compounds of structure 3 can be prepared starting from the respective compounds of structure 6 (Ru represents methyl) by the following sequence
- Deprotection of the silyl ether derivative using a fluorinated agent such as TBAF in a solvent such as THF at a temperature about rt; and
- Oxidation of the alcohol to the corresponding ketone under standard oxidative conditions using reagents such as MnO$_2$, pyridinium chlorochromate or NMO/TPAP in a solvent such as AcCN or CH$_2$Cl$_2$ at a temperature about rt;

Alternatively compounds of structure 3 can be prepared starting from the respective compounds of structure 6 (Ru represents hydrogen) by the following sequence:
- deprotection of the silyl ether derivative using a fluorinated agent such as TBAF in a solvent such as THF at a temperature about rt;
- Oxidation of the alcohol to the corresponding aldehyde under standard oxidative conditions using reagents such as MnO$_2$, pyridinium chlorochromate or NMO/TPAP in a solvent such as AcCN or CH$_2$Cl$_2$ at a temperature about rt;
- Addition of an alkyl Grignard reagent at a temperature below rt (preferably about −78° C.) in a solvent such as THF, or, alternatively, addition of a trialkylaluminum reagent at a temperature about 0° C. in a solvent such as CH$_2$Cl$_2$ providing the corresponding secondary alcohol; and
- Oxidation of the alcohol under standard oxidative conditions using reagents such as TPAP/NMO or MnO$_2$ in a solvent such as CH$_2$Cl$_2$ or AcCN at a temperature about rt to provide the compound of structure 3.

Structure 6

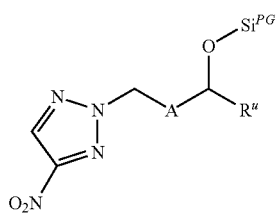

Compounds of structure 4 may be prepared by reacting Ms-O—CH$_2$-A-C(OR$^x$)$_2$—CH$_3$ or Cl—CH$_2$-A-C(OR$^x$)$_2$—CH$_3$ with 4-nitro-2H-[1,2,3]triazole in the presence of a base such as K$_2$CO$_3$ or Cs$_2$CO$_3$ in a solvent such as acetone or AcCN at a temperature about rt or 80° C. (with or without addition of tetrabutylammonium bromide) using, in case A represents furan-2,5-diyl, an appropriate protected furan derivative such as 2-(5-chloromethyl-furan-2-yl)-2-methyl-[1,3]dioxolane or, in case A represents thiophen-2,5-diyl, an appropriate protected thiophene derivative such as 2-(5-chloromethyl-thiophen-2-yl)-2-methyl-[1,3]dioxolane or, in case A represents thiazol-2,4-diyl, an appropriate protected thiazole derivative such as methanesulfonic acid 4-(2-methyl-[1,3]dioxolan-2-yl)-thiazol-2-ylmethyl ester or 4-chloromethyl-2-(2-methyl-[1,3]dioxolan-2-yl)-thiazole or, in case A represents thiophen-2,4-diyl, an appropriate protected thiophene derivative such as 2-(4-chloromethyl-thiophen-2-yl)-2-methyl-[1,3]dioxolane or 2-(5-chloromethyl-thiophen-3-yl)-2-methyl-[1,3]dioxolane or, in case A represents thiazol-2,5-diyl, an appropriate protected thiazole derivative such as methanesulfonic acid 5-(2-methyl-[1,3]dioxolan-2-yl)-thiazol-2-ylmethyl ester or 5-chloromethyl-2-(2-methyl-[1,3]dioxolan-2-yl)-thiazol or, in case A represents oxazole-2,5-diyl, an appropriate protected oxazole derivative such as 2-chloromethyl-5-(2-methyl-[1,3]dioxolan-2-yl)-oxazole, or another appropriate reagent of formula Ms-O—CH$_2$-A-C (OR$^x$)$_2$—CH$_3$ or Cl—CH$_2$-A-C(OR$^x$)$_2$—CH$_3$. Alternatively, the reaction may be performed in the presence of a base such as DIPEA in a solvent such as DMF, acetone or a mixture of both at a temperature about rt or 50° C.

Compounds of structure 5 may be prepared by reacting Ms-O—CH$_2$-A-C(O)—O—R or Cl—CH$_2$-A-C(O)—O—R with 4-nitro-2H-[1,2,3]triazole in analogy to those of structure 4 using, for instance, a commercially available 5-chloromethyl-furan-2-carboxylic acid methyl ester (A represents furan-2,5-diyl), or 4-chloromethyl-thiazole-2-carboxylic acid ethyl ester (A represents thiazol-2,4-diyl).

Compounds of structure 6 may be prepared by reacting Ms-O—CH$_2$-A-CH(OSi$^{PG}$)—R$^u$ or Cl—CH$_2$-A-CH(OSi$^{PG}$)—R$^u$ with commercially available 4-nitro-2H-[1,2,3]triazole in analogy to those of structure 4 using, in case A represents oxazole-2,5-diyl, an oxazole derivative such as 2-[1-(tert-butyl-dimethyl-silanyloxy)-ethyl]-5-chloromethyl-oxazole or, in case A represents oxazole-2,4-diyl, an appropriate protected oxazole derivative such as methanesulfonic acid 2-(tert-butyl-dimethyl-silanyloxymethyl)-oxazol-4-ylmethyl ester, or another appropriate reagent of formula Ms-O—CH$_2$-A-CH(OSi$^{PG}$)—R$^u$ or Cl—CH$_2$-A-CH(OSi$^{PG}$)—R$^u$.

1-(5-Chloromethyl-furan-2-yl)-ethanone may be prepared using the following sequence: a) protection of commercially available 5-hydroxymethyl-2-furaldehyde using 3,4-dihydro-2H-pyran in the presence of pyridinium toluene-4-sulfonate in a solvent such as CH$_2$Cl$_2$; b) methylation of the aldehyde using for example methylmagnesium chloride in a solvent such as THF at a temperature about 0° C.; c) oxidation of the resulting secondary alcohol using an oxidizing agent such as MnO$_2$ in a solvent such as CH$_2$Cl$_2$ at a temperature about 45° C.; d) removal of the protecting group using an acid such as Amberlyst 15 in a suitable solvent such as MeOH at a temperature about 35° C.; and e) chlorination of the alcohol using for example Ms-Cl in the presence of a base such as Et$_3$N and DMAP in a solvent such as CH$_2$Cl$_2$ at a temperature ranging from 0° C. to rt.

2-(5-Chloromethyl-furan-2-yl)-2-methyl-[1,3]dioxolane may be prepared using the following sequence: a) protection of commercially available 1-furan-2-yl-ethanone in the presence of trimethylorthoformate and a catalyst such as LiBF$_4$ in a solvent such as ethylene glycol at a temperature about 95° C.; b) lithiation with an organolithium reagent such as n-butyl lithium in a solvent such as THF at a temperature about −78° C. and subsequent addition of DMF; c) reduction with a reducing agent such as NaBH$_4$ in a solvent such as MeOH at a temperature about 0° C.; and d) chlorination of the alcohol using for example methanesulfonyl chloride in the presence of a base such as Et$_3$N and DMAP in a solvent such as CH$_2$Cl$_2$ at a temperature about 0° C.

1-(5-Chloromethyl-isoxazol-3-yl)-ethanone may be prepared using the following sequence: a) protection of 5-hydroxymethyl-isoxazole-3-carboxylic acid ethyl ester using for example tert-butyldimethylsilyl chloride in the presence of a base such as imidazole in a solvent such as THF; b) reduction with a reducing agent such as DiBAL in a solvent such as THF at a temperature below rt; c) oxidation of the alcohol under standard oxidative conditions using reagents such as MnO$_2$ in a solvent such as AcCN at a temperature about rt; d) addition of trimethylaluminum at a temperature about 0° C. in a solvent such as CH$_2$Cl$_2$; e) oxidation of the alcohol under standard oxidative conditions using reagents such as MnO$_2$ in a solvent such as AcCN at a temperature about rt; f) deprotection of the silyl ether derivative using a fluorinated agent such as TBAF in a solvent such as THF at a temperature about rt; and g) chlorination of the alcohol using for example methanesulfonyl chloride in the presence of a base such as Et$_3$N and DMAP in a solvent such as CH$_2$Cl$_2$ at a temperature about 0° C.

2-(5-Chloromethyl-thiophen-2-yl)-2-methyl-[1,3]dioxolane may be prepared using the following sequence: a) lithiation of commercially available 2-methyl-2-thiophen-2-yl-[1,3]dioxolane with an organolithium reagent such as n-butyl lithium in the presence of N,N,N',N'-tetramethyl-ethylenediamine in a solvent such as THF at a temperature about −78° C. and subsequent addition of DMF; b) reduction with a reducing agent such as NaBH$_4$ in a solvent such as MeOH at a temperature about 0° C.; and c) chlorination of the alcohol using for example methanesulfonyl chloride in the presence of a base such as Et$_3$N and DMAP in a solvent such as CH$_2$Cl$_2$ at a temperature about 0° C.

Methanesulfonic acid 4-(2-methyl-[1,3]dioxolan-2-yl)-thiazol-2-ylmethyl ester may be prepared by the following sequence: a) reaction of commercially available 2,4-dibromo-thiazole with an organolithium reagent such as n-butyl lithium in a solvent such as ether at a temperature about −78° C. and subsequent formylation with N,N-dimethyl-formamide at a temperature ranging from −78° C. to rt; b) reduction with a reducing agent such as NaBH$_4$ in a solvent such as MeOH at a temperature about rt; c) protection of the alcohol using tert-butyldimethylsilyl chloride in the presence of a base such as imidazole in a solvent such as dichloromethane; d) reaction of the protected alcohol with an organolithium reagent such as n-butyl lithium in a solvent such as ether at a temperature about −78° C. and subsequent acetylation with N,N-dimethylacetamide at a temperature ranging from −78° C. to rt; e) ketal formation in the presence of trimethylorthoformate and a catalyst such as LiBF$_4$ in a solvent such as ethylene glycol at a temperature about 95° C.; f) deprotection of the silyl protecting group under standard conditions such as TBAF in a solvent such as THF at a temperature about rt or 0° C.; and g) mesylation using a reagent such as methanesulfonyl chloride in a solvent such as CH$_2$Cl$_2$ in the presence of a base such as Et$_3$N and DMAP at a temperature about 0° C.

2-(4-Chloromethyl-thiophen-2-yl)-2-methyl-[1,3]dioxolane may be prepared as described for 2-(5-chloromethyl-furan-2-yl)-2-methyl-[1,3]dioxolane but starting with commercially available 1-(4-bromo-2-thienyl)-ethan-1-one.

4-Chloromethyl-thiazole-2-carboxylic acid ethyl ester may be prepared by the following sequence: a) reaction of commercially available oxalamic acid ethyl ester with Lawesson's reagent in a solvent such as toluene at a temperature about 80° C.; and b) cyclization with 1,3-dichloroacetone in a solvent such as toluene at a temperature about 110° C.

4-Chloromethyl-2-(2-methyl-[1,3]dioxolan-2-yl)-thiazole may be prepared from 4-chloro-methyl-thiazole-2-carboxylic acid ethyl ester by the sequence described for the synthesis of compounds of structure 3 from compounds of structure 5 followed by ketal formation in the presence of trimethylorthoformate and a catalyst such as LiBF$_4$ in a solvent such as ethylene glycol at a temperature about 90° C.

Methanesulfonic acid 5-(2-methyl-[1,3]dioxolan-2-yl)-thiazol-2-ylmethyl ester may be prepared by the following sequence: a) reaction of commercially available 2-bromo-thiazole-5-carbaldehyde with trimethylaluminum in a solvent such as dichloromethane at a temperature about 0° C.; b) oxidation with an oxidative agent such as MnO$_2$ in a solvent such as acetonitrile at a temperature about rt; c) ketal formation in the presence of trimethylorthoformate and a catalyst such as LiBF$_4$ in a solvent such as ethylene glycol at a temperature about 95° C.; d) lithiation with an organolithium reagent such as n-butyl lithium in a solvent such as ether at a temperature about −78° C. and subsequent formylation with N,N-dimethylformamide; e) reduction with a reducing agent such as NaBH$_4$ in a solvent such as MeOH at a temperature about rt; and f) mesylation using a reagent such as methanesulfonyl chloride in a solvent such as CH$_2$Cl$_2$ in the presence of a base such as Et$_3$N and DMAP at a temperature about 0° C.

5-Chloromethyl-2-(2-methyl-[1,3]dioxolan-2-yl)-thiazole may be prepared by the following sequence: a) reduction of commercially available 2-bromo-thiazole-5-carbaldehyde with a reducing agent such as NaBH$_4$ in a solvent such as MeOH at a temperature about rt; b) protection of the alcohol using tert-butyldimethylsilyl chloride in a solvent such as CH$_2$Cl$_2$ in the presence of a base such as imidazole; c) lithiation with an organolithium reagent such as n-butyl lithium in a solvent such as ether at a temperature about −78° C. and subsequent acetylation with N,N-dimethylacetamide; d) ketal formation in the presence of trimethylorthoformate and a catalyst such as LiBF$_4$ in a solvent such as ethylene glycol at a temperature about 95° C.; e) deprotection of the silyl ether derivative using a fluorinated agent such as TBAF in a solvent such as THF at a temperature about rt; and f) chlorination using a reagent such as methanesulfonyl chloride in a solvent such as CH$_2$Cl$_2$ in the presence of a base such as Et$_3$N and DMAP at a temperature about 0° C.

2-(5-Chloromethyl-thiophen-3-yl)-2-methyl-[1,3]dioxolane may be prepared as described for 5-chloromethyl-2-(2-methyl-[1,3]dioxolan-2-yl)-thiazole but starting with commercially available 4-bromo-thiophene-2-carbaldehyde.

Methanesulfonic acid 4-acetyl-oxazol-2-ylmethyl ester may be prepared by the following sequence: a) oxazole formation reacting commercially available 3-phenyl-acrylamide with 3-bromo-2-oxo-propionic acid ethyl ester in the presence of a base such as NaHCO$_3$ in a solvent such as THF at a temperature around 60° C.; b) oxidative cleavage using for example silica gel supported NaIO$_4$ and a metal complex such as RuC$_{1-3}$ hydrate in a solvent such as dichloromethane at a temperature about rt; c) reduction with a reducing agent such as NaBH$_4$ in a solvent such as EtOH at a temperature about 0° C.; d) protection of the alcohol using tert-butyldimethylsilyl chloride in a solvent such as CH$_2$Cl$_2$ in the presence of a base such as imidazole; e) reduction to the aldehyde with a reducing agent such as DiBAL in a solvent such as CH$_2$Cl$_2$ at a temperature about −78° C.; f) reaction with trimethylaluminum in a solvent such as dichloromethane at a temperature about 0° C.; g) oxidation with an oxidative agent such as MnO$_2$ in a solvent such as acetonitrile at a temperature about rt; h) deprotection of the silyl ether derivative using a fluorinated agent such as TBAF in a solvent such as THF at a temperature about rt; and i) mesylation using a reagent such as methanesulfonyl chloride in a solvent such as CH$_2$Cl$_2$ in the presence of a base such as Et$_3$N and DMAP at a temperature about 0° C.

Methanesulfonic acid 2-(tert-butyl-dimethyl-silanyloxymethyl)-oxazol-4-ylmethyl ester may be prepared by the following sequence: a) oxazole formation reacting commercially available 3-phenyl-acrylamide with 3-bromo-2-oxo-propionic acid ethyl ester in the presence of a base such as NaHCO$_3$ in a solvent such as THF at a temperature around 60° C.; b) oxidative cleavage using for example silica gel supported NaIO$_4$ and a metal complex such as RuCl$_3$ hydrate in a solvent such as CH$_2$Cl$_2$ at a temperature about rt; c) reduction with a reducing agent such as NaBH$_4$ in a solvent such as EtOH at a temperature about 0° C.; d) protection of the alcohol using tert-butyldimethylsilyl chloride in a solvent such as CH$_2$Cl$_2$ in the presence of a base such as imidazole; e) reduction to the alcohol with a reducing agent such as DiBAL in a solvent such as THF at a temperature about 0° C.; and f) mesylation using a reagent such as methanesulfonyl chloride in a solvent such as CH$_2$Cl$_2$ in the presence of a base such as Et$_3$N and DMAP at a temperature about 0° C.

2-[1-(tert-Butyl-dimethyl-silanyloxy)-ethyl]-5-chloromethyl-oxazole may be prepared using the following sequence: a) reaction of commercially available oxazole with an organomagnesium reagent such as isopropylmagnesium chloride in a solvent such as THF at a temperature about −15° C. and subsequent acetylation with N-methoxy-N-methylacetamide at a temperature ranging from −15° C. to rt; b) reduction with a reducing agent such as NaBH$_4$ in a solvent such as MeOH at a temperature about rt; c) protection of the alcohol using tert-butyldimethylsilyl chloride in the presence of a base such as imidazole in a solvent such as THF; d) reaction of the protected alcohol with an organolithium reagent such as t-butyl lithium in a solvent such as THF at a temperature ranging from −78° C. to −40° C. and subsequent formylation with N,N-dimethyl-formamide at a temperature ranging from −78° C. to rt; e) reduction with a reducing agent such as NaBH$_4$ in a solvent such as MeOH at a temperature about rt; and f) chlorination using a reagent such as methanesulfonyl chloride in a solvent such as CH$_2$Cl$_2$ in the presence of a base such as Et$_3$N and DMAP at a temperature about 0° C.

2-Chloromethyl-5-(2-methyl-[1,3]dioxolan-2-yl)-oxazole may be prepared using the following sequence: a) lithiation of commercially available oxazole with an organolithium reagent such as n-butyl lithium in a solvent such as THF at a temperature about −78° C. and subsequent addition of DMF; b) reduction with a reducing agent such as NaBH$_4$ in a solvent such as MeOH at a temperature about 0° C.; c) protection of the alcohol using tert-butyldimethylsilyl chloride in the presence of a base such as imidazole in a solvent such as THF; d) lithiation with an organolithium reagent such as t-butyl lithium in a solvent such as THF at a temperature ranging from −78° C. to −40° C. and subsequent formylation with DMF at a temperature ranging from −78° C. to rt; e) reaction with trimethylaluminum in a solvent such as dichloromethane at a temperature about 0° C.; f) oxidation with an oxidative agent such as MnO$_2$ in a solvent such as acetonitrile at a temperature about rt; g) ketal formation and deprotection of the silyl protection group in the presence of trimethylorthoformate and a catalyst such as LiBF$_4$ in a solvent such as ethylene glycol at a temperature about 95° C.; and h) chlorination of the alcohol using for example methanesulfonyl chloride in the presence of a base such as Et$_3$N and DMAP in a solvent such as CH$_2$Cl$_2$ at a temperature about 0° C.

(2-(1,1-difluoroethyl)oxazol-4-yl)methyl methanesulfonate may be prepared using the sequence described in the experimental part.

Acids of structure 7 are commercially available, well known in the art or prepared according to the methods described below.

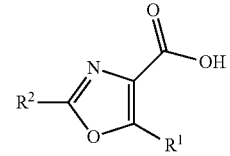

Structure 7

Compounds of structure 7 wherein R$^2$ represents Me may be prepared as described in Scheme 1 by reacting 3-oxo-propionic acid ester derivatives with an aqueous solution of sodium nitrite in presence of an acid such as glacial acetic acid. Subsequent transformation of the oxime with acetic anhydride in presence of an acid such as glacial acetic acid and catalytic amounts of metal chlorides such as mercury chloride or zinc chloride and zinc powder followed by cyclization under dehydrating conditions such as thionyl chloride in chloroform followed by saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 1: Oxazole synthesis (1).

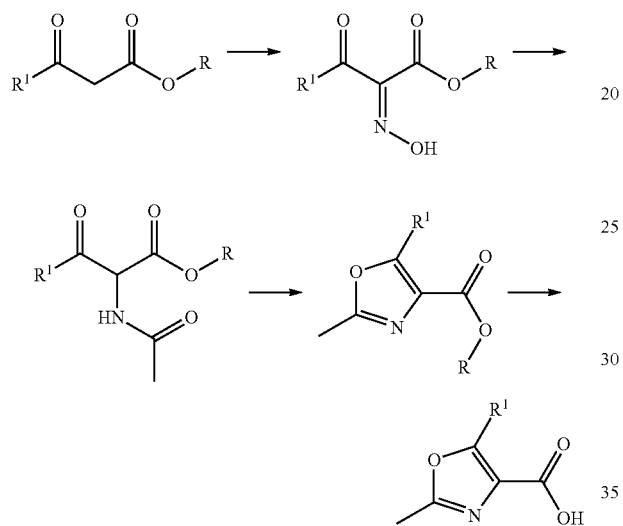

Alternatively, compounds of structure 7 may be prepared as described in Scheme 2 by reacting 3-oxo-propionic acid ester derivatives with a solution of 4-acetamido-benzenesulfonyl azide and a base such as Et$_3$N. Subsequent treatment with a carboxamide derivative and a catalyst such as tetrakis(acetato)dirhodium(II) dihydrate followed by cyclization using triphenylphosphine and iodine in the presence of a base such as Et$_3$N afforded the respective ester derivative. Saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 2: Oxazole synthesis (2).

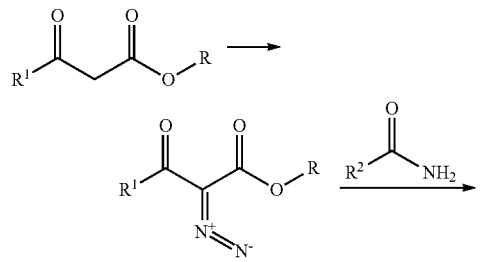

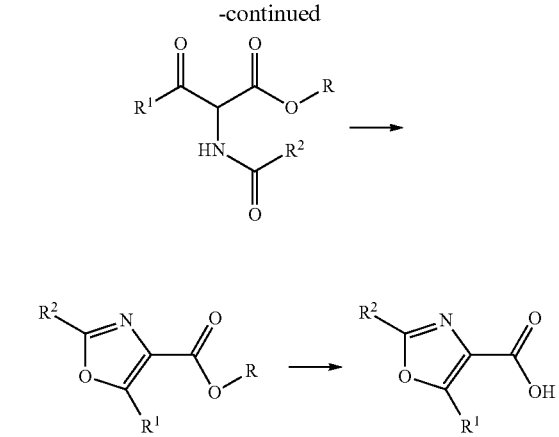

Alternatively, compounds of structure 7 wherein $R^2$ represents hydrogen may be prepared as described in Scheme 2b by reacting a solution of an acid derivative of formula $R^1$COOH with methyl isocyanoacetate in the presence of a base such as potassium carbonate sesquihydrate or DIPEA and DPPA in a solvent such as DMF. Saponification of the ester function using methods known in the art such as treatment with a base such as NaOH in a solvent or a solvent mixture such as ethanol/water or THF afforded the respective acid derivative. The respective acids $R^1$COOH are commercially available or well known in the art.

Scheme 2b: Oxazole synthesis (3).

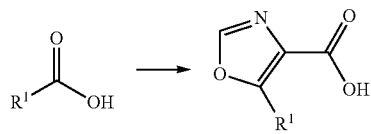

Alternatively, compounds of structure 7 may be prepared as described in Scheme 3 by esterification of a 3-phenylserine derivative using a reagent such as thionylchloride in a solvent such as MeOH at a temperature about 0° C. followed by coupling with a carboxylic acid derivative $R^2$—COOH using standard conditions such as HOBt, DCC, N-methylmorpholine in a solvent such as CH$_2$Cl$_2$ at a temperature about 0° C. Oxidation of the alcohol with an oxidative reagent such as Dess-Martin periodinane in a solvent such as CH$_2$Cl$_2$ followed by cyclization using triphenylphosphine and iodine in the presence of a base such as Et$_3$N afforded the respective oxazole derivative. The desired acid derivatives may be obtained by saponification of the ester function using methods known in the art such as treatment with a base such as aq. LiOH in a solvent such as dioxane.

Scheme 3: Oxazole synthesis (4).

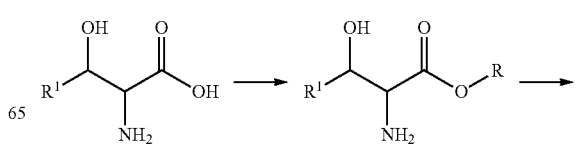

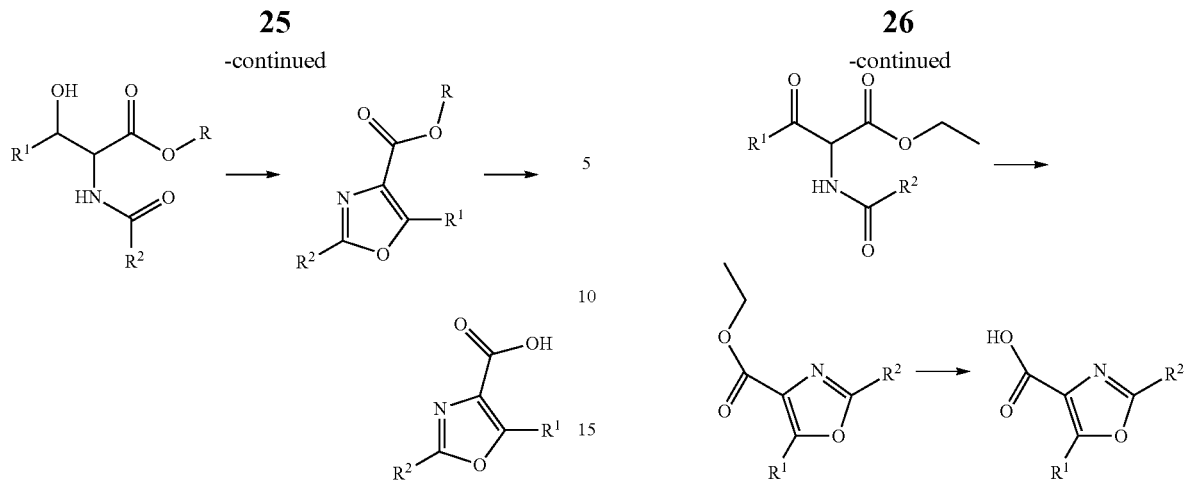

Alternatively, compounds of structure 7 may be prepared as described in Scheme 4 using the following sequence: a) formation of an acid chloride by treatment of a suitable acid of formula $R^1COOH$ with oxalyl chloride and catalytic DMF in a solvent such as 1,2-dichloroethane at a temperature around rt; b) cyclization of the resulting acide chloride in a solvent such as THF using ethyl isocyanoacetate in the presence of a base such as $Et_3N$ and DMAP at a temperature of about 75° C.; c) opening of the resulting oxazole using acetylchloride in a solvent such as EtOH at a temperature between 10 and 85° C.; d) reaction of the amine with an anhydride of formula $R^2C(O)$—O—$C(O)R^2$ in the presence of a base such as sodium acetate in a solvent such as water. Alternatively, the amine may be reacted with an appropriate acid chloride of formula $R^2C(O)Cl$ in the presence of a base such as triethylamine; e) cyclization upon addition of an acid such as conc. sulphuric acid at a temperature around rt; and f) saponification of the ester function using methods known in the art such as treatment with a base such as aq. NaOH in a solvent such as THF.

Scheme 4: Oxazole synthesis (5).

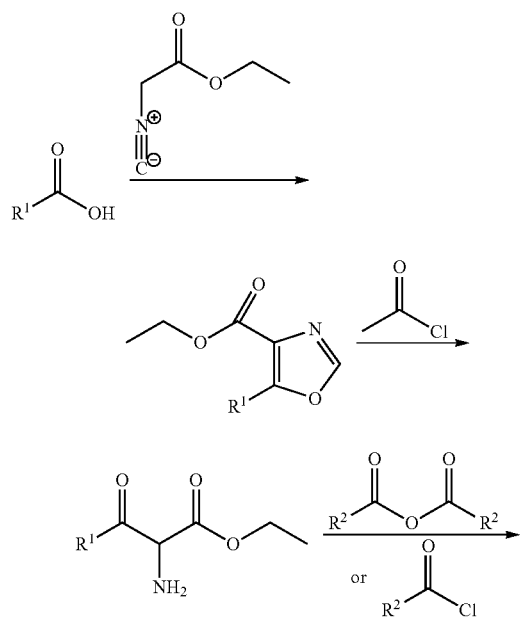

EXPERIMENTAL PART

Abbreviations (as used herein and in the description above)
Ac acetyl
AcCl acetyl chloride
AcCN acetonitrile
AcOH acetic acid
$AlMe_3$ trimethyl aluminium
aq. aqueous
atm atmosphere
Boc tert-butoxycarbonyl
bp boiling point
BSA bovine serum albumin
Bu butyl
BuLi n-butyllithium
ca. about
cat. catalytic
Cbz benzyloxycarbonyl
COAD chronic obstructive airway disease
COLD chronic obstructive lung disease
COPD chronic obstructive pulmonary disease
DAD diode array detector
DC dendritic cells
DCC N,N'-dicyclohexylcarbodiimide
PL-DCC polymer supported N,N'-dicyclohexylcarbodiimide
DCE 1,2-dichloroethane
DIPEA diisopropylethylamine
DiBAL di-iso-butylaluminum hydride
DMAP 4-N,N-dimethylaminopyridine
DMEM dulbecco's modified eagle's medium
DMF dimethylformamide
DMSO dimethylsulfoxide
DPPA diphenyl phosphoryl azide
EA ethyl acetate
$EC_{50}$ half maximal effective concentration
EIA enzyme immunoassay
EDC N-(3-dimethylaminopropyl)-N'-ethyl-carbodiimide hydrochloride
ELSD evaporative light-scattering detection
eq. equivalent(s)
ES+ electro-spray, positive ionization
Et ethyl
Ether or $Et_2O$ diethylether
$Et_3N$ triethylamine
EtOH ethanol
FA formic acid
FAD familial autosomic dominant
FC flash column chromatography on silica gel FLIPR fluorescence imaging plate reader
FPRL1 formyl-peptide receptor like-1
FPRL2 formyl-peptide receptor like-2
GSH glutathione
h hour(s)
HATU 2-(7-aza-1H-benzotriazol-1-yl)-1,1,3,3-tetramethyluronium hexafluorophosphate
HBTU O-(benzotriazol-1-yl)-N,N,N',N'-tetramethyluronium hexafluorophosphate
HBSS hanks' balanced salt solution
hept heptane
HIV human immunodeficiency virus
HLM human liver microsomes
HOBt hydroxybenzotriazole
HOAt 7-aza-1-hydroxybenzotriazole
HPLC high performance liquid chromatography
IU international units
LC-MS liquid chromatography—mass spectrometry
lem emission wavelength
lex excitation wavelength
LPS lipopolysaccharide
m-CPBA meta-chloroperbenzoic acid
Me methyl
MeOH methanol
min minute(s)
mM millimolar
µM micromolar
mRNA messenger ribonucleic acid
MPLC medium pressure liquid chromatography
MS mass spectrometry
Ms methanesulfonyl
NADPH nicotinamide adenine dinucleotide phosphate
nm nanometer
nM nanomolar
NMO N-methyl-morpholine-N-oxide
NMR nuclear magnetic resonance
OAc acetate
org. organic
p para
p-TsOH para-toluene sulfonic acid
PG protecting group
PL-Deta polystyrene supported diethylenetriamine
PL-HCO3 polystyrene supported hydrogen carbonate, version MP (macro porous)
PTFE polytetrafluoroethylene
PyBOP benzotriazol-1-yl-oxy-tris-pyrrolidino-phosphonium-hexafluoro-phosphate
Rochelle's salt potassium sodium tartrate
RCP radiochemical purity
rf retention factor
rpm rotation per minute
rt room temperature
sat. saturated
SCX strong cation exchanger
SDS sodium dodecyl sulfate
Si-DCC silica bound DCC from silicycle
sol. solution
TBA tetra-n-butylammonium
TBAF tetra-n-butylammonium fluoride
TBME tert-butyl methyl ester
TBDMS tert-butyl-dimethyl-silyl
TBDPS tert-butyl-diphenyl-silyl
TBTU O-(benzotriazol-1-yl)-N,N,N',N'-tetramethyluronium tetrafluoroborate
tBu tert-butyl, tertiary butyl
TFA trifluoroacetic acid
THF tetrahydrofuran
TIPS tri-isopropyl-silyl
TLC thin layer chromatography
TMS trimethyl-silyl
TPAP tetrapropylammonium perruthenate
$t_R$ retention time
TsOH p-toluene sulfonic acid monohydrate
UV ultra violet
V is visible I Chemistry General. All temperatures are stated in degrees Celsius (° C.). Unless otherwise indicated, the reactions take place at rt.

As SCX material SiliaBond® SCX from Silicycle was used.

As polymer supported DCC, PL-DCC from Polymer Laboratories was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, $CH_2Cl_2$, $CHCl_3$, MeOH or mixtures thereof.

MPLC were performed using isolute SPE Flash SI II columns from international sorbent technology, elution with EA, $Et_2O$, hept, hexane, $CH_2Cl_2$, $CHCl_3$, MeOH, $NH_4OH$ or mixtures thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 µm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 µm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 05c (if not indicated otherwise): Analytical: Dionex GHP 3200 Binary Pump, MS: Thermo MSQ Plus, DAD: Dionex PDA 3000, ELSD: Sedere Sedex 85. Column: Zorbax SB-AQ 1.8 µm, 4.6×20 mm ID from Agilent Technologies, thermostated in the Dionex TCC-3200 compartment. Eluents: A: $H_2O$+0.04% TFA; B: AcCN. Method: Gradient: 5% B→95% B over 1 min. Flow: 4.5 mL/min. Detection: UV/Vis and/or ELSD, and MS, $t_R$ is given in min.

LC-MS-conditions 06 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis C18 2.7 µm, 3×30 mm ID from Sigma-Aldrich, thermostated in the Dionex TCC-3000 compartment. Eluents: A: $H_2O$+0.05% TFA; B: AcCN. Method: Gradient: 5% B→95% B over 2.40 min. Flow: 3.0 mL/min. Detection: UV/Vis and/or ELSD, and MS, $t_R$ is given in min.

LC-MS-conditions 07 (if not indicated otherwise): Analytical: Dionex HGP-3200RS Binary Pump, MS: Thermo MSQ Plus, DAD: Dionex DAD-3000RS, ELSD: Sedere Sedex 85. Column: Zorbax SB-AQ 4.6×50 mm ID from Agilent Technologies, thermostated in the Dionex TCC-3200 compartment (40° C.). Eluents: A: $H_2O$+0.04% TFA; B:

AcCN. Method: Gradient: 5% B→95% B over 1 min. Flow: 4.5 mL/min. Detection: UV/Vis and/or ELSD, and MS, $t_R$ is given in min.

LC-MS-conditions 08 (if not indicated otherwise): Analytical: Dionex HPG-3000 Binary Pump, MS: Thermo MSQ MS, DAD: Dionex PDA 3000, ELSD: PolymerLab ELS 2100. Column: XBridge C18 2.5 μm, 2.1×20 mm, thermostated in the Dionex TCC-3000 compartment (50° C.). Eluents: A: $H_2O$+0.05% TFA; B: AcCN. Method: Gradient: 5% B→95% B over 2.00 min. Flow: 1.4 mL/min. Detection: UV/Vis and/or ELSD, and MS, $t_R$ is given in min.

HPLC preparative: X-Bridge C18 5 μm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD, and MS, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

GENERAL PROCEDURES

General procedure A

Amide Coupling

In a flame dried round-bottomed flask equipped with a magnetic stir bar and under an inert atmosphere ($N_2$), a 0.2M solution of the acid (1.0 eq.), in $CH_2Cl_2$ was treated with DMAP (0.25 eq.), HOBt (1.2 eq.), EDC (2.5 or 1.0 eq.) and DIPEA (4.0 eq.) and the resulting mixture was stirred at rt for 30 min. A 0.2M solution of the aminotriazole derivative (1.0 eq.) in $CH_2Cl_2$ was added and the resulting reaction mixture was stirred at rt overnight. $CH_2Cl_2$ was added and the org. phase was washed with water and brine. The org. phase was dried over $Na_2SO_4$, filtered, and the solvents were removed under reduced pressure. Purification of the residue by FC or HPLC gave the desired compound.

General Procedure E

Ester Hydrolysis

A 0.5M solution of the respective carboxylic acid ester (1.0 eq.) in a 3:1 mixture of THF and the corresponding alkyl alcohol, e.g. MeOH or EtOH, was treated with 1M aq. NaOH (2.0 eq.). After stirring for 3 h, a white suspension was formed and the org. volatiles were removed under reduced pressure. The remaining mixture was diluted with water (half the amount of the 3:1 mixture of THF and MeOH), cooled with an ice-bath and acidified (pH=3-4) by addition of 1M aq. HCl. The suspension was filtered and the residue was washed with cold water to afford the desired carboxylic acid derivative after drying.

General Procedure F

Synthesis of 2-acetylamino-3-oxo-propionic acid ester derivatives

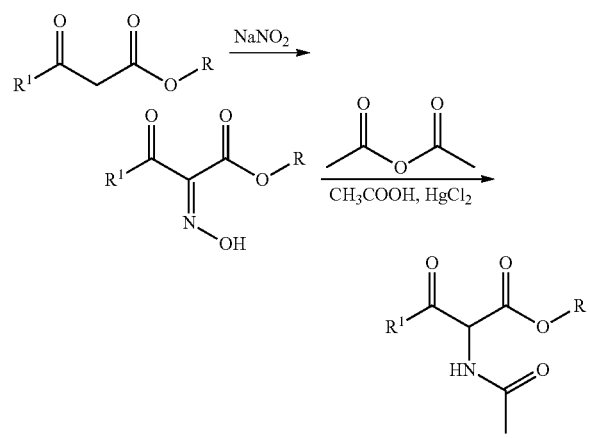

In a flame dried round-bottomed flask equipped with a magnetic stir bar and under inert atmosphere ($N_2$), a 2.5M solution of the respective 3-oxo-propionic acid ester derivative (1.0 eq.) in glacial acetic acid was cooled to 10° C. and at this temperature was added a 8.2M solution of $NaNO_2$ (1.16 eq.) in water. After the addition was complete (15 min), the solution was allowed to warm to rt and stirred for 2 h. The solution was then poured into water (5.3 times the volume of glacial acetic acid) and after a few minutes crystals begun to appear. This suspension was cooled with an ice-bath and crystals were collected by filtration. The cake was washed several times with cold water and the water was removed by azeotrope distillation with toluene under reduced pressure to give the respective 2-hydroxyimino-3-oxo-propionic acid ester derivative, which was dissolved in a 1:1.3 mixture of acetic anhydride and glacial acetic acid (0.66 mL for 1.0 mmol of the respective 3-oxo-propionic acid ester derivative). To this solution was added sodium acetate (0.06 eq.) and $HgCl_2$ (0.002 eq.). The mixture was refluxed for 1 h, then cooled to rt and filtered. The solid was rinsed with ether, the organic filtrate was recovered, washed 3 times with water and once with 1M aq. $K_2CO_3$. The organic layer was dried over $MgSO_4$, filtered and the solvent was removed under reduced pressure. The crude product was purified by FC to afford the desired 2-acetylamino-3-oxo-propionic acid ester derivative.

General Procedure G

Cyclization (1)

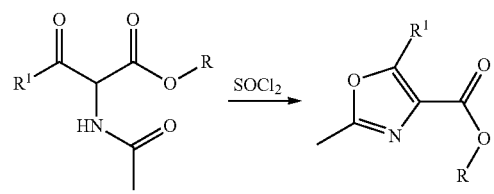

In a flame dried round-bottomed flask equipped with a magnetic stir bar and under inert atmosphere ($N_2$), a 1.6M solution of the respective 2-acetylamino-3-oxo-propionic acid ester derivative (1.0 eq.) in chloroform was cooled to about 0° C. in an ice/NaCl bath. SOCl$_2$ (1.4 eq.) was added to the stirred solution and the temperature was maintained at about 0° C. for 30 minutes. Then the solution was stirred at reflux for one hour. Another 0.25 eq. of SOCl$_2$ was added and the reaction mixture was refluxed for an additional hour. The excess SOCl$_2$ was quenched with 1M aq. K$_2$CO$_3$. The aq. layer was extracted twice with ether. The combined organic phases were washed once with water and dried over MgSO$_4$, filtered and the solvent was removed under reduced pressure to afford the desired oxazole derivative which might be purified by FC.

General Procedure H

Cyclization (2)

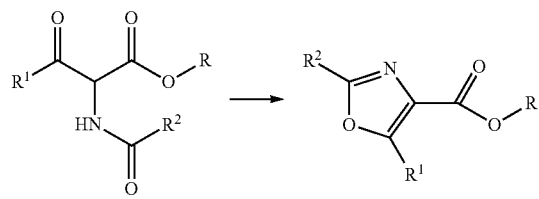

In a flame dried round-bottomed flask equipped with a magnetic stir bar and under an inert atmosphere (N$_2$), Et$_3$N (4.1 eq.) followed by a 0.1M solution of the respective 2-(carbonyl-amino)-3-oxo-propionic acid ester derivative (1.0 eq.) in CH$_2$Cl$_2$ were added to a 0.2M solution of triphenylphosphine (2.0 eq.), and iodine (2.0 eq.) in CH$_2$Cl$_2$. The reaction mixture was stirred for 1.5 h at rt. The solvent was removed under reduced pressure and the residue purified by FC to afford the desired oxazole derivative.

General Procedure I

N-Insertion

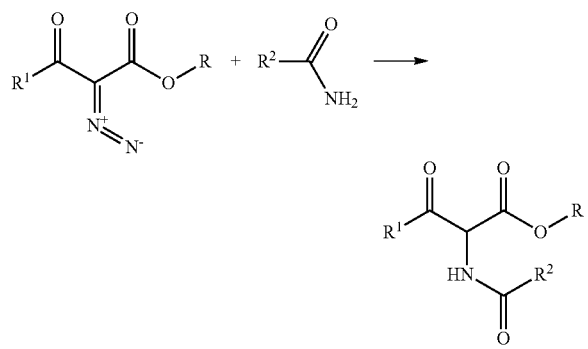

In a flame dried round-bottomed flask equipped with a magnetic stir bar and under an inert atmosphere (N$_2$), a 0.5M solution of the diazo derivative (1.0 eq.) in 1,2-dichloroethane was added over 1.5 h to a refluxing solution of the carboxamide derivative (1.0 eq.) and rhodium(II) acetate (tetrakis (acetato)dirhodium(II) dihydrate, 0.05 eq.) in 1,2-dichloroethane (3 mL per mmol of carboxamide derivative). The reaction mixture was then stirred for 1.5 h at reflux. The solvent was removed under reduced pressure and the residue purified by FC to afford the desired 2-(carbonyl-amino)-3-oxo-propionic acid ester derivative.

General Procedure J

Diazotation

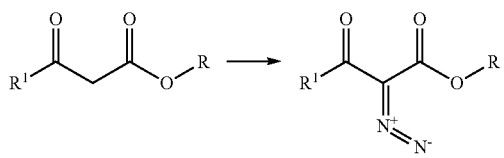

In a flame dried round-bottomed flask equipped with a magnetic stir bar and under an inert atmosphere (N$_2$), a 0.17M solution of the 3-oxo-propionic acid ester derivative (1.0 eq.) in AcCN was treated at 0° C. with 4-acetamidobenzenesulfonyl azide (1.0 eq.) followed by Et$_3$N (3.0 eq.). The reaction mixture was stirred for 1 h at rt. The solvent was removed under reduced pressure, the residue triturated in ether-light petroleum and filtered. The solvent was removed under reduced pressure and the residue was purified by FC to afford the desired diazo derivative.

General Procedure K

Claisen Condensation

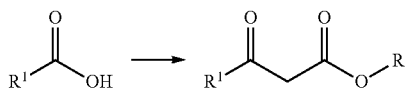

A) In a flame dried round-bottomed flask equipped with a magnetic stir bar and under an inert atmosphere (N$_2$), a 1.3M solution of the acid derivative (1.0 eq.) in 1,2-dichloroethane was treated at rt with a few drops of DMF followed by oxalyl chloride (1.3 eq.). The reaction mixture was stirred for 3 h at rt followed by 20 min at 80° C. The solvent was removed under reduced pressure.

B) In a flame dried round-bottomed flask equipped with a magnetic stir bar and under an inert atmosphere (N$_2$), a 0.83M solution of potassium malonic acid monoethyl ester (2 eq.) in acetonitrile was treated at 10° C. with magnesium chloride (2.5 eq.) and the suspension was stirred at 10° C. for 30 min and at rt for 3 h. The reaction mixture was cooled to 0° C. and treated dropwise over 15 min with the solution of the acid chloride prepared under A, followed by Et$_3$N (2 eq.). The resulting suspension was stirred at rt for 20 h. The solvent was removed under reduced pressure and the residue was striped with toluene. The residue was taken in toluene (1.5 mL per mmol of potassium malonic acid monoethyl ester) and treated at 10° C. with the same amount of 4M HCl as of toluene. The organic layer was washed twice with 4M HCl, water, dried over MgSO$_4$,

General Procedure M

Cyclization (3)

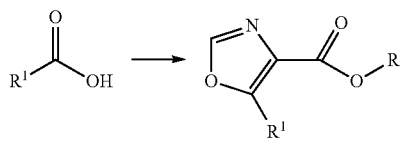

In a flame dried round-bottomed flask equipped with a magnetic stir bar and under an inert atmosphere (N$_2$), a 0.5M solution of the acid (1.0 eq.) in DMF was treated at rt with potassium carbonate sesquihydrate or, alternatively DIPEA (from 1.2 eq. to 1.5 eq.) followed by a 2.0M solution of methyl isocyanoacetate (from 1.5 eq. to 3.2 eq.) in DMF and the mixture was stirred at rt for 5 min. The reaction mixture was cooled to 0° C. and treated with a 0.67M solution of DPPA (1.1 eq.) in DMF. The resulting suspension was stirred at 0° C. for 2 h and at rt for 15 h. It was then poured in a 1:1 mixture of EA and toluene and the organic layer was washed with water, 10% citric acid, water and sat. aq. NaHCO$_3$. The organic layer was dried over MgSO$_4$, filtered, and the solvent was removed under reduced pressure. The residue was purified by FC to afford the desired derivative.

General Procedure N

Cyclization (4)

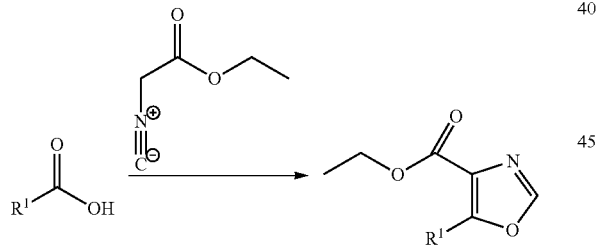

A) In a flame dried round-bottomed flask equipped with a magnetic stir bar and under an inert atmosphere (N$_2$), a 1.0M solution of the acid derivative (1.0 eq.) in 1,2-dichloroethane was treated at rt with a few drops of DMF followed by oxalyl chloride (1.3 eq.). The reaction mixture was stirred for 3 h at rt followed by 20 min at 80° C. The solvent was removed under reduced pressure.

B) In a flame dried round-bottomed flask equipped with a magnetic stir bar and under an inert atmosphere (N$_2$), a 0.7M solution of ethyl isocyanoacetate (1 eq.) in THF was treated with DMAP (0.1 eq.) and Et$_3$N (2.2 eq.) and the reaction mixture was heated to 60° C. before dropwise addition of a THF solution (⅕ of the volume used for the ethyl isocyanoacetate solution) of the acid chloride prepared under A. and the mixture was then stirred at 75° C. for 1.5 h. 25% HCl followed by TBDME were added. The organic layer was washed with sat. aq. NaHCO$_3$, dried over MgSO$_4$, filtered, and the solvent was removed under reduced pressure. The residue was purified by FC to afford the desired derivative.

General Procedure O

Oxazole Opening and N-acetylation

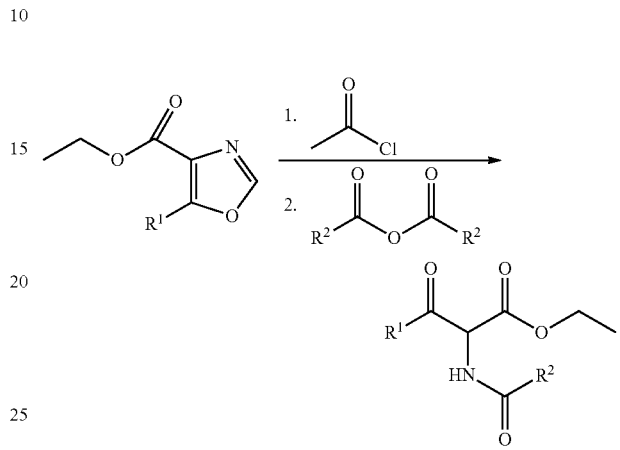

In a flame dried round-bottomed flask equipped with a magnetic stir bar and under an inert atmosphere (N$_2$), a 0.43M solution of the oxazole derivative (1.0 eq.) in EtOH was treated at 0° C. with acetylchlorid (9 eq.) while maintaining the temperature below 10° C. The reaction mixture was then stirred overnight at 50° C. The solvent was removed under reduced pressure and the residue was treated at 0° C. with a 1.3M solution of sodium acetate (2 eq) in water. The anhydride (2 eq.) was then added dropwise. After 30 min, TBDME was added and the organic phase was washed with water, dried over Na$_2$SO$_4$, filtered, and the solvent was removed under reduced pressure. The residue was purified by FC to afford the desired derivative.

General Procedure P

Cyclization (5)

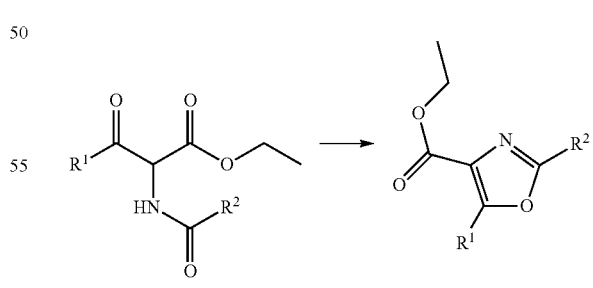

In a flame dried round-bottomed flask equipped with a magnetic stir bar and under an inert atmosphere (N$_2$), a 0.65M solution of the amide in conc. Sulphuric acide was stirred overnight at rt. The reaction mixture was then poured onto ice and extracted several time with 4-methyl-3-pentanone. The combined organic phases were dried over Na$_2$SO$_4$, filtered, and the solvent was removed under reduced pressure. The residue might be purified by FC to afford the desired derivative.

General Procedure Q

Synthesis of 2-acetylamino-3-oxo-propionic acid ester derivatives

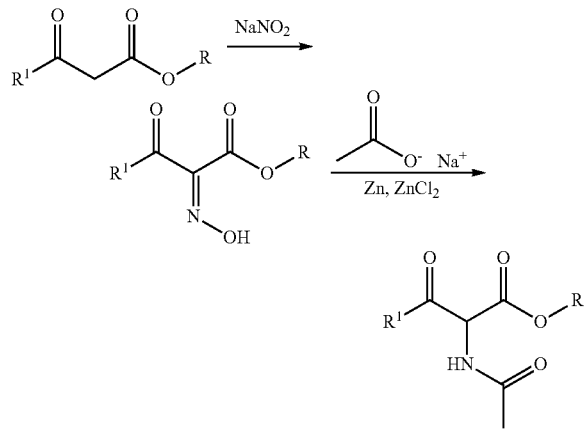

In a flame dried round-bottomed flask equipped with a magnetic stir bar and under inert atmosphere ($N_2$), a 2.5M solution of the respective 3-oxo-propionic acid ester derivative (1.0 eq.) in glacial acetic acid was cooled to 10° C. and at this temperature was added a 8.2M solution of $NaNO_2$ (1.16 eq.) in water. After the addition was complete (15 min), the solution was allowed to warm to rt and stirred for 2 h. The solution was then poured into water (5.3 times the volume of glacial acetic acid) and after a few minutes crystals begun to appear. This suspension was cooled with an ice-bath and crystals were collected by filtration. The cake was washed several times with cold water and the water was removed by azeotrope distillation with toluene under reduced pressure to give the respective 2-hydroxyimino-3-oxo-propionic acid ester derivative, which was dissolved in a acetic anhydride (3.0 eq.) and acetic acid (1 mL per gram of the respective 2-hydroxyimino-3-oxo-propionic acid ester derivative). To this solution was added sodium acetate (0.06 eq.) and $ZnCl_2$ (0.002 eq.). The mixture was then treated portionwise over 15 min with Zn powder (3.0 eq). The reaction mixture was refluxed for 0.5 h, then cooled to rt and filtered. The solid was rinsed with ether, the organic filtrate was recovered, washed 3 times with water and once with 1M aq. $K_2CO_3$. The organic layer was dried over $MgSO_4$, filtered and the solvent was removed under reduced pressure to afford the desired 2-acetylamino-3-oxo-propionic acid ester derivative.

General Procedure Z2

Amide Coupling

Into vials, containing the acid (0.15 mmol) dissolved in DMF/DCM 1/1 (500 µL) was put 0.5 eq. of 1M HOAT in DMF (50 µL; 0.05 mmol) and 2 eq Si-Carbodiimide (Si-DCC) 1.08 mmol/g. Then amines (1 eq) dissolved in DMF/DCM 1/1 (200 µL) were added. The mixtures were stirred one night at rt. PL-DETA resin 2 eq was added in each vials and the mixtures were stirred 22 h at rt. 2 ml of DCM/DMF 1/1 were added to the reaction mixtures and it was put on preconditioned syringes (1 g PL-$HCO_3$ and 1 mL DCM) which were washed with 2 ml DCM/MeOH (1/1), 3 ml MeOH and 2 ml DCM/MeOH (1/1). The solvents were removed under reduced pressure. Purification of the residue by HPLC gave the desired compound.

Synthesis of Intermediates

4-Bromo-thiazole-2-carbaldehyde

In a flame dried round-bottomed flask equipped with a magnetic stir bar and under inert atmosphere ($N_2$), a solution of commercially available 2,4-dibromo-thiazole (3.50 g, 14.41 mmol) in dry $Et_2O$ (120 mL) was treated with n-BuLi (5.9 mL of a 2.5M solution in hexanes, 14.72 mmol) at −78° C. The reaction mixture was stirred at this temperature for 30 min. N,N-Dimethylformamide (1.35 mL, 14.47 mmol) was then added and the mixture allowed to warm to rt over a period of 1 h. The reaction was quenched by the addition of sat. aq. $NH_4Cl$ (50 mL). The layers were separated and the aq. layer extracted with $Et_2O$ (3×50 mL). The combined org. extracts dried over $Na_2SO_4$, filtered, and the solvents were removed under reduced pressure. Purification of the residue by FC (10:1->3:1 hept-EA) gave the title compound as a pale yellow solid. TLC:rf(1:1 hept-EA)=0.21. LC-MS-conditions 02: $t_R$=0.81 min.

(4-Bromo-thiazol-2-yl)-methanol

In a flame dried round-bottomed flask equipped with a magnetic stir bar and under inert atmosphere ($N_2$), 4-bromo-thiazole-2-carbaldehyde (1.68 g, 8.75 mmol) was dissolved in MeOH (10 mL). $NaBH_4$ (428 mg, 10.86 mmol) was added portionwise at 0° C. and the reaction mixture stirred at rt for 1 h. Water (10 mL) was added and the mixture extracted with EA (3×20 mL). The combined org. extracts were dried over $Na_2SO_4$, filtered, and the solvents were removed under reduced pressure. Purification of the residue by FC (6:1->2:1 hept-EA) gave the title compound as a pale yellow solid. TLC:rf (1:1 hept-EA)=0.31. LC-MS-conditions 02: $t_R$=0.62 min $[M+H]^+$=194.31.

4-Bromo-2-(tert-butyl-dimethyl-silanyloxymethyl)-thiazole

In a flame dried round-bottomed flask equipped with a magnetic stir bar and under inert atmosphere ($N_2$), (4-bromo-thiazol-2-yl)-methanol (1.37 g, 7.06 mmol) was dissolved in dry $CH_2Cl_2$ (21 mL). tert-Butyldimethylsilyl chloride (1.17 g, 7.77 mmol) was added at 0° C. followed by imidazole (985 mg, 14.47 mmol). The reaction mixture was stirred at rt for 2 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure to give the title compound as a colorless oil. TLC:rf (1:1 hept-EA)=0.80.

1-[2-(tert-Butyl-dimethyl-silanyloxymethyl)-thiazol-4-yl]-ethanone

In a flame dried round-bottomed flask equipped with a magnetic stir bar and under inert atmosphere ($N_2$), to a solution of 4-bromo-2-(tert-butyl-dimethyl-silanyloxymethyl)-thiazole (1.94 g, 6.29 mmol) in dry $Et_2O$ (50 mL) was added n-BuLi (2.76 mL of a 2.5M solution in hexanes, 6.92 mmol) at −78° C. The reaction mixture was then stirred for 30 min at −78° C. before N,N-dimethylacetamide (1.17 mL, 12.58 mmol) was added dropwise. The reaction mixture was allowed to warm up to rt over a period of 1 h and stirred at this temperature for 20 min. Sat. aq. NH$_4$Cl (20 mL) was added, the layers separated and the aq. layer extracted with Et$_2$O (3×30 mL). The combined org. extracts were dried over Na$_2$SO$_4$, filtered, and the solvent was removed under reduced pressure. Purification of the residue by FC (20:1->5:1 hept-EA) gave the title compound as a yellow solid. TLC:rf (1:1 hept-EA)=0.51. LC-MS-conditions 02: $t_R$=1.11 min; [M+H]$^+$=272.39.

2-(tert-Butyl-dimethyl-silanyloxymethyl)-4-(2-methyl-[1,3]dioxolan-2-yl)-thiazole In a flame dried round-bottomed flask equipped with a magnetic stir bar and under inert atmosphere (N$_2$), a solution of 1-[2-(tert-butyl-dimethyl-silanyloxymethyl)-thiazol-4-yl]-ethanone (1.77 g, 6.52 mmol) in ethylene glycol (7 mL) was treated with trimethylorthoformate (1.46 mL, 13.29 mmol) followed by LiBF$_4$ (125 mg, 1.30 mmol). The reaction mixture was heated at 95° C. for 4 h. Sat. aq. Na$_2$CO$_3$ (5 mL) was added and the mixture was extracted with Et$_2$O (2×20 mL). The org. extracts were dried over Na$_2$SO$_4$, filtered, and the solvent was removed under reduced pressure. Purification of the residue by FC (20:1->3:1 hept-EA) gave the title compound as a brown oil. TLC:rf (1:1 hept-EA)=0.56. LC-MS-conditions 02: $t_R$=1.11 min; [M+H]$^+$=316.36.

[4-(2-Methyl-[1,3]dioxolan-2-yl)-thiazol-2-yl]-methanol

In a flame dried round-bottomed flask equipped with a magnetic stir bar and under inert atmosphere (N$_2$), a solution of 2-(tert-butyl-dimethyl-silanyloxymethyl)-4-(2-methyl-[1,3]dioxolan-2-yl)-thiazole (1.30 g, 4.12 mmol) in dry THF (10 mL) was treated at 0° C. with TBAF (6.2 mL of a 1M solution in THF, 6.20 mmol). The reaction mixture was stirred at 0° C. for 5 min and at rt for 1 h30. The mixture was then diluted with EA (10 mL), washed with brine (3×10 mL), dried over MgSO$_4$, filtered and concentrated under reduced pressure. Purification of the residue by FC (5:1->1:3 hept-EA) gave the title compound as a yellow oil. TLC:rf (1:2 hept-EA)=0.20. LC-MS-conditions 02: $t_R$=0.59 min; [M+H]$^+$=202.48.

2-[4-(2-Methyl-[1,3]dioxolan-2-yl)-thiazol-2-ylmethyl]-4-nitro-2H-[1,2,3]triazole In a flame dried round-bottomed flask equipped with a magnetic stir bar and under inert atmosphere (N$_2$), a solution of [4-(2-methyl-[1,3]dioxolan-2-yl)-thiazol-2-yl]-methanol (18.460 g, 91.73 mmol) in dry CH$_2$Cl$_2$ (300 mL) was treated at 0° C. with Et$_3$N (16.59 mL, 118.62 mmol) followed by DMAP (1.132 g, 9.17 mmol) and Ms-Cl (9.17 mL, 115.83 mmol). After stirring at 0° C. for 1 h, the reaction was quenched with water (80 mL). The layers were separated and the aq. layer extracted with CH$_2$Cl$_2$ (3×) The org. layer was dried over MgSO$_4$, filtered, and the solvents were removed under reduced pressure to give crude methanesulfonic acid 4-(2-methyl-[1,3]dioxolan-2-yl)-thiazol-2-ylmethyl ester as a brown oil. Part of this crude material (2.756 g, 9.87 mmol) in DMF (20 mL) was added to a solution of 4-nitro-2H-[1,2,3]triazole (10.60 g of a 10% solution in acetone, 9.29 mmol) in DMF (20 mL) pre-treated for 30 min with DIPEA (3.18 mL, 18.59 mmol) and the reaction mixture was stirred overnight at 50° C. Water (25 mL), followed by EA (50 mL) were added. The aq. layer was extracted with EA (50 mL) and the combined org. extracts were dried over Na$_2$SO$_4$, filtered, and the solvents were removed under reduced pressure. Purification of the residue by FC (1:2 hept-EA) gave the title compound as a yellow solid: TLC:rf (1:2 hept-EA)=0.52. LC-MS-conditions 02: $t_R$=0.88 min, [M+H]$^+$=297.84.

1-[2-(4-Nitro-[1,2,3]triazol-2-ylmethyl)-thiazol-4-yl]-ethanone

In a flame dried round-bottomed flask equipped with a magnetic stir bar and under inert atmosphere (N$_2$), a solution of 2-[4-(2-methyl-[1,3]dioxolan-2-yl)-thiazol-2-ylmethyl]-4-nitro-2H-[1,2,3]triazole (2.360 g, 7.94 mmol) in THF (40.0 mL) was treated with 1N HCl (21.4 mL, 21.4 mmol) and the reaction mixture was stirred at rt overnight. The reaction mixture was neutralized with 1N NaOH. The aq. layer was extracted twice with EA (20 mL) and the combined org. extracts were dried over MgSO$_4$, filtered, and the solvents were removed under reduced pressure. Purification of the residue by FC (6:4 hept-EA) gave the title compound as a yellow solid: TLC:rf (6:4 hept-EA)=0.29. LC-MS-conditions 02: $t_R$=0.81 min, [M+H]$^+$=254.35.

2-[4-(1,1-Difluoro-ethyl)-thiazol-2-ylmethyl]-4-nitro-2H-[1,2,3]triazole

In a flame dried round-bottomed flask equipped with a magnetic stir bar and under inert atmosphere (N$_2$), 1-[2-(4-nitro-[1,2,3]triazol-2-ylmethyl)-thiazol-4-yl]-ethanone (1.000 g, 3.95 mmol) was treated with Deoxo-Fluor (17.47 g of a 50% solution in toluene, 39.49 mmol) followed by EtOH (0.2 mL). The reaction mixture was stirred at 60° C. overnight. The reaction mixture was poured on sat. aq. Na$_2$CO$_3$ (60 mL). The aq. layer was extracted twice with EA (60 mL) and the combined org. extracts were washed with sat. aq. Na$_2$CO$_3$ (60 mL), water (60 mL) dried over MgSO$_4$, filtered, and the solvents were removed under reduced pressure. Purification of the residue by FC (7:3 hept-EA) gave the title compound as an orange solid: TLC:rf (7:3 hept-EA)=0.32. LC-MS-conditions 02: $t_R$=0.96 min.

2-[4-(1,1-Difluoro-ethyl)-thiazol-2-ylmethyl]-2H-[1,2,3]triazol-4-ylamine

In a flame dried round-bottomed flask equipped with a magnetic stir bar and under inert atmosphere (N$_2$), a mixture of 2-[4-(1,1-difluoro-ethyl)-thiazol-2-ylmethyl]-4-nitro-2H-[1,2,3]triazole (491 mg, 1.78 mmol), iron powder (302 mg, 5.35 mmol) and NH$_4$Cl (482 mg, 8.92 mmol) in a mixture of EtOH (8.0 mL) and water (4.0 mL) was stirred at 85° C. for 20 min. The reaction mixture was filtered while hot and concentrated under reduced pressure. CH$_2$Cl$_2$ (20 mL) was added followed by water (20 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil. LC-MS-conditions 02: $t_R$=0.76 min; [M+H]$^+$=246.16.

(E)-2-Styryl-oxazole-4-carboxylic acid ethyl ester

In a flame dried round-bottomed flask equipped with a magnetic stir bar and under inert atmosphere (N$_2$), a suspension of 3-phenyl-acrylamide (10.31 g, 67.95 mmol) and NaHCO$_3$ (28.47 g, 339.73 mmol) in THF (260 mL) was treated with 3-bromo-2-oxo-propionic acid ethyl ester (13.04 mL, 88.33 mmol) and the reaction mixture was heated at reflux for 15 h. 3-Bromo-2-oxo-propionic acid ethyl ester (13.04 mL, 88.33 mmol) was added again and the reaction mixture was stirred at reflux for 15 h. The reaction mixture was then filtered over celite and the solvents were evaporated under reduced pressure. The residue was dissolved in THF (30 mL) and treated at 0° C., dropwise, with trifluoroacetic anhydride (30.0 mL, 215.83 mmol). The reaction mixture was then stirred at rt overnight. Sat. aq. $Na_2CO_3$ was added and the mixture was extracted with EA (3×150 mL), dried over $MgSO_4$, filtered, and the solvent was removed under reduced pressure. Purification of the residue by FC (1:9 EA-Hept) gave the title compound as a yellow solid. TLC:rf (1:9 EA-Hept)=0.1. LC-MS-conditions 02: $t_R$=1.01 min; $[M+H]^+$=244.48.

2-Formyl-oxazole-4-carboxylic acid ethyl ester

In a flame dried round-bottomed flask equipped with a magnetic stir bar and under inert atmosphere ($N_2$), a solution of $NaIO_4$ (3.21 g, 15.00 mmol) in water (26.0) mL was slowly added to a vigorously stirred suspension of silica gel (15.0 g) in acetone (60.0 mL). The mixture was then concentrated under reduced pressure and the lumpy solid slurred in $CH_2Cl_2$ and the solvent was evaporated under reduced pressure. $CH_2Cl_2$ (40.0 mL) was added and the reaction mixture was treated at rt with (E)-2-styryl-oxazole-4-carboxylic acid ethyl ester (1.22 g, 5.00 mmol) and $RuCl_3$ hydrate (82 mg, 0.15 mmol). The reaction mixture was stirred at rt in the dark for 30 min, filtered and concentrated under reduced pressure. Purification of the residue by FC (1:9 to 1:2 EA-Hept) gave the title compound as a yellow solid. TLC:rf (3:2 EA-Hept)=0.21. LC-MS-conditions 02: $t_R$=0.51 min; $[M+H_2O+H]^+$=188.50.

2-Hydroxymethyl-oxazole-4-carboxylic acid ethyl ester

In a flame dried round-bottomed flask equipped with a magnetic stir bar and under inert atmosphere ($N_2$), 2-formyl-oxazole-4-carboxylic acid ethyl ester (272 mg, 1.61 mmol) was dissolved in EtOH (5.0 mL). $NaBH_4$ (112 mg, 2.84 mmol) was added portionwise at 0° C. and the reaction mixture stirred at 0° C. for 1 h. Sat. aq. $NH_4Cl$ was added and the mixture extracted with EA (5×10 mL). The combined org. extracts were dried over $Na_2SO_4$, filtered, and the solvents were removed under reduced pressure to give the title compound as a yellow oil. TLC: rf (EA)=0.50. LC-MS-conditions 02: $t_R$=0.58 min; $[M+H]^+$=172.03.

2-(tert-Butyl-dimethyl-silanyloxymethyl)-oxazole-4-carboxylic acid ethyl ester

In a flame dried round-bottomed flask equipped with a magnetic stir bar and under inert atmosphere ($N_2$), 2-hydroxymethyl-oxazole-4-carboxylic acid ethyl ester (275 mg, 1.61 mmol) was dissolved in dry $CH_2Cl_2$ (5.0 mL). tert-Butyldimethylsilyl chloride (510 mg, 3.22 mmol) was added at rt followed by imidazole (221 mg, 3.22 mmol). The reaction mixture was stirred at rt for 30 min. Water was added, the layers were separated and the org. layer was dried over $Na_2SO_4$, filtered, and the solvent removed under reduced pressure. Purification of the residue by FC (1:20 to 1:9 EA-Hept) gave the title compound as a colorless oil. TLC:rf (9:1 hept-EA)=0.15. LC-MS-conditions 02: $t_R$=1.10 min; $[M+H]^+$=286.38.

2-(tert-Butyl-dimethyl-silanyloxymethyl)-oxazole-4-carbaldehyde

In a flame dried round-bottomed flask equipped with a magnetic stir bar and under inert atmosphere ($N_2$), a solution of 2-(tert-butyl-dimethyl-silanyloxymethyl)-oxazole-4-carboxylic acid ethyl ester (283 mg, 0.99 mmol) in $CH_2Cl_2$ (5.0 mL) was treated at −78° C. with DiBAL (1.85 mL of a 1M sol in toluene, 1.85 mmol) and the reaction mixture was stirred for 1 h at −78° C. MeOH (70 μL) and $H_2O$ (100 μL) were added and the reaction mixture was allowed to warm to rt. The reaction mixture was filtered, and the solvent removed under reduced pressure to give the title compound as a colorless oil. TLC:rf (1:1 hept-EA)=0.61. LC-MS-conditions 02: $t_R$=1.03 min; $[M+H_2O+H]^+$=260.50.

1-[2-(tert-Butyl-dimethyl-silanyloxymethyl)-oxazol-4-yl]-ethanol

In a flame dried round-bottomed flask equipped with a magnetic stir bar and under inert atmosphere ($N_2$), a solution of 2-(tert-butyl-dimethyl-silanyloxymethyl)-oxazole-4-carbaldehyde (223 mg, 0.92 mmol) in $CH_2Cl_2$ (8.0 mL) was treated at 0° C. with trimethylaluminum (2.50 mL of a 2M solution in toluene, 5.00 mmol). The reaction mixture was then stirred at 0° C. for 45 min. Sat. aq. $NH_4Cl$ was then added and the aq. layer was extracted twice with $CH_2Cl_2$ and twice with EA. The combined org. extracts were dried over $Na_2SO_4$, filtered, and the solvents were removed under reduced pressure to give the title compound as a colorless oil. TLC:rf (1:1 hept-EA)=0.32. LC-MS-conditions 02: $t_R$=0.97 min, $[M+H]^+$=258.30.

1-[2-(tert-Butyl-dimethyl-silanyloxymethyl)-oxazol-4-yl]-ethanone

In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanol (193 mg, 0.75 mmol) in AcCN (5.0 mL) was treated at rt with $MnO_2$ (362 mg, 3.75 mmol). The reaction mixture was stirred for 16 h at rt before being filtered through Celite. The solvent was removed under reduced pressure to give the title compound as a white solid. TLC:rf (1:1 hept-EA)=0.69. LC-MS-conditions 02: $t_R$=1.04 min, $[M+H]^+$=255.84.

1-(2-Hydroxymethyl-oxazol-4-yl)ethanone

In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanone (192 mg, 0.75 mmol) in dry THF (5.0 mL) was treated at rt with TBAF (1.1 mL of a 1M solution in THF, 1.10 mmol). The reaction mixture was stirred at rt for 1.5 h. The mixture was then diluted with EA (10 mL), washed with brine (3×10 mL), dried over $Na_2SO_4$, filtered and concentrated under reduced pressure. Purification of the residue by FC (1:1 to 2:1 EA-Hept) gave the title compound as a pale yellow solid. TLC: rf (EA)=0.37. LC-MS-conditions 02: $t_R$=0.34 min, $[M+H]^+$=142.46.

Methanesulfonic acid 4-acetyl-oxazol-2-ylmethyl ester

In a flame dried round-bottomed flask equipped with a magnetic stir bar and under inert atmosphere ($N_2$), a solution of 1-(2-hydroxymethyl-oxazol-4-yl)-ethanone (75 mg, 0.53 mmol) in dry $CH_2Cl_2$ (5.0 mL) was treated at 0° C. with $Et_3N$ (0.10 mL, 0.71 mmol) followed by DMAP (6 mg, 0.05 mmol) and Ms-Cl (0.05 mL, 0.66 mmol). After stirring at 0° C. for 30 min, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give the title compound as a yellow oil. TLC: rf (EA)=0.63. LC-MS-conditions 02: t$_R$=0.64 min; [M+H]$^+$=220.22.

1-[2-(4-Nitro-[1,2,3]triazol-2-ylmethyl)-oxazol-4-yl]-ethanone

In a flame dried round-bottomed flask equipped with a magnetic stir bar and under inert atmosphere (N$_2$), a solution of methanesulfonic acid 4-acetyl-oxazol-2-ylmethyl ester (116 mg, 0.53 mmol) in DMF (3.0 mL) was added to a solution of 4-nitro-2H-[1,2,3]triazole (62 mg, 0.53 mmol) in DMF (2.0 mL) pre-treated for 30 min with DIPEA (0.20 mL, 1.17 mmol) and the reaction mixture was stirred for 20 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (3:1 to 1:1 hept-EA) gave the title compound as a yellow solid. TLC:rf (1:2 hept-EA)=0.49. LC-MS-conditions 01: t$_R$=0.76 min.

2-[4-(1,1-Difluoro-ethyl)-oxazol-2-ylmethyl]-4-nitro-2H-[1,2,3]triazole

In a flame dried round-bottomed flask equipped with a magnetic stir bar and under inert atmosphere (N$_2$), 1-[2-(4-nitro-[1,2,3]triazol-2-ylmethyl)-oxazol-4-yl]-ethanone (170 mg, 0.72 mmol) was treated with Deoxo-Fluor (3.17 g of a 50% solution in toluene, 7.17 mmol) followed by EtOH (0.2 mL). The reaction mixture was stirred at for 16 h. The reaction mixture was poured on sat. aq. Na$_2$CO$_3$ (5 mL). The aq. layer was extracted twice with dichloromethane (6 mL) and the combined org. extracts were washed with sat. aq. Na$_2$CO$_3$ (6 mL), water (6 mL) dried over MgSO$_4$, filtered, and the solvents were removed under reduced pressure. Purification of the residue by FC (1000:12.2:1 to 1000:100:8 CH$_2$Cl$_2$—MeOH—NH$_4$OH) gave the title compound as a yellow oil: TLC:rf (1:2 hept-EA)=0.58. LC-MS-conditions 05c: t$_R$=0.45 min.

2-[4-(1,1-Difluoro-ethyl)-oxazol-2-ylmethyl]-2H-[1,2,3]triazol-4-ylamine

In a flame dried round-bottomed flask equipped with a magnetic stir bar and under inert atmosphere (N$_2$), a mixture of 2-[4-(1,1-difluoro-ethyl)-oxazol-2-ylmethyl]-4-nitro-2H-[1,2,3]triazole (130 mg, 0.50 mmol), iron powder (85 mg, 1.41 mmol) and NH$_4$Cl (136 mg, 2.51 mmol) in a mixture of EtOH (2.0 mL) and water (1.0 mL) was stirred at 70° C. for 60 min. The reaction mixture was filtered while hot and concentrated under reduced pressure. CH$_2$Cl$_2$ (10 mL) was added followed by water (10 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil. LC-MS-conditions 05c: t$_R$=0.47 min.

1-(5-Hydroxymethyl-furan-2-yl)-ethanone

In a flame dried round-bottomed flask under inert atmosphere (N$_2$), to a mixture of 5-hydroxymethyl-2-furaldehyde (100 g, 0.79 mol) and pyridinium toluene-4-sulfonate (10 g, 0.04 mol) in CH$_2$Cl$_2$ (1 L) was added 3,4-dihydro-2H-pyran (150 mL, 1.62 mol) while keeping the internal temperature below 28° C. (water bath). The reaction mixture was stirred at rt for 5 h. Water (1 L) was added, the layers separated and the org. layer washed with water (500 mL) and evaporated to dryness to give crude 5-(tetrahydro-pyran-2-yloxymethyl)-furan-2-carbaldehyde as a yellow oil (171 g, quant.).

Crude 5-(tetrahydro-pyran-2-yloxymethyl)-furan-2-carbaldehyde (171 g) was dissolved in THF (1 L) and cooled to 1° C. Methylmagnesium chloride (3 M in THF, 325 mL, 0.97 mol) was then added while keeping the internal temperature below 5° C. After the addition, the reaction mixture was stirred at rt for 1 h. Water (1 L), TBME (1 L) and 40% aq. citric acid (200 mL) were added, the layers separated and the org. layer washed with water (500 mL) and evaporated to dryness to give 174 g of crude 1-[5-(tetrahydro-pyran-2-yloxymethyl)-furan-2-yl]-ethanol (95% yield). Part of the crude material (96 g, 0.43 mol) was dissolved in CH$_2$Cl$_2$ (1 L) and treated with MnO$_2$ (371 g, 4.26 mol) at rt. The reaction mixture was heated to 45° C. and stirred at this temperature for 24 h. The mixture was then filtered over celite and the filter cake washed with CH$_2$Cl$_2$. The filtrate was evaporated to dryness to give crude 1-[5-(tetrahydro-pyran-2-yloxymethyl)-furan-2-yl]-ethanone (89 g, 93%) as a yellow oil.

Crude 1-[5-(tetrahydro-pyran-2-yloxymethyl)-furan-2-yl]-ethanone (89 g, 0.40 mol) was dissolved in MeOH (500 mL) and treated with Amberlyst 15 (15 g) at rt. The reaction mixture was stirred at 35° C. for 1 h, cooled to rt and filtered over celite. Et$_3$N (1 mL) was added and the mixture was evaporated to dryness. The residue was stripped with methylcyclohexane and 1-(5-hydroxymethyl-furan-2-yl)-ethanone (55 g, 99%) was obtained as a yellow oil that solidified on standing.

1-[5-(4-Nitro-[1,2,3]triazol-2-ylmethyl)-furan-2-yl]-ethanone

In a flame dried round-bottomed flask equipped with a magnetic stir bar and under inert atmosphere (N$_2$), a solution of 1-(5-hydroxymethyl-furan-2-yl)-ethanone (2.00 g, 14.27 mmol) in dry CH$_2$Cl$_2$ (29 mL) was treated at 0° C. with Et$_3$N (2.58 mL, 18.55 mmol) followed by DMAP (178 mg, 1.43 mmol) and Ms-Cl (1.33 mL, 17.13 mmol). After stirring at rt for 3 h, the reaction was quenched with water. The layers were separated and the aq. layer extracted with CH$_2$Cl$_2$ (3×) The org. layer was dried over MgSO$_4$, filtered, and the solvents were removed under reduced pressure to give 3.93 g (quant.) of crude 1-(5-chloromethyl-furan-2-yl)-ethanone as a brown oil. Part of this crude material (1.718 g, 10.83 mmol) in DMF (10.3 mL) was added to a solution of 4-nitro-2H-[1,2,3]triazole (10.30 g of a 10% solution in acetone, 9.03 mmol) in DMF (10.3 mL) pre-treated for 30 min with DIPEA (3.09 mL, 18.06 mmol) and the reaction mixture was stirred overnight at 50° C. Water (32 mL), followed by EA (65 mL) were added. The aq. layer was extracted with EA (65 mL) and the combined org. extracts were dried over Na$_2$SO$_4$, filtered, and the solvents were removed under reduced pressure. Purification of the residue by FC (2:1 hept-EA) gave the title compound as a yellow solid: TLC:rf (2:1 hept-EA)=0.20. LC-MS-conditions 02: t$_R$=0.85 min, [M+H]$^+$=237.46.

2-[5-(1,1-Difluoro-ethyl)-furan-2-ylmethyl]-4-nitro-2H-[1,2,3]triazole

In a flame dried round-bottomed flask equipped with a magnetic stir bar and under inert atmosphere (N$_2$), 1-[5-(4-nitro-[1,2,3]triazol-2-ylmethyl)-furan-2-yl]-ethanone (1.000 g, 4.23 mmol) was treated with Deoxo-Fluor (18.73 g of a 50% solution in toluene, 42.34 mmol) followed by EtOH (0.2 mL). The reaction mixture was stirred at for 2 days. The reaction mixture was poured on sat. aq. $Na_2CO_3$ (50 mL). The aq. layer was extracted twice with dichloromethane (60 mL) and the combined org. extracts were washed with sat. aq. $Na_2CO_3$ (60 mL), water (60 mL) dried over $MgSO_4$, filtered, and the solvents were removed under reduced pressure. Purification of the residue by FC (7:3 hept-EA) gave the title compound as an orange solid: TLC:rf (7:3 hept-EA)=0.42. LC-MS-conditions 02: $t_R$=1.00 min.

2-[5-(1,1-Difluoro-ethyl)-furan-2-ylmethyl]-2H-[1,2,3]triazol-4-ylamine

In a flame dried round-bottomed flask equipped with a magnetic stir bar and under inert atmosphere ($N_2$), a mixture of 2-[5-(1,1-difluoro-ethyl)-furan-2-ylmethyl]-4-nitro-2H-[1,2,3]triazole (471 mg, 1.82 mmol), iron powder (309 mg, 5.47 mmol) and $NH_4Cl$ (493 mg, 9.12 mmol) in a mixture of EtOH (7.0 mL) and water (3.5 mL) was stirred at 85° C. for 20 min. The reaction mixture was filtered while hot and concentrated under reduced pressure. $CH_2Cl_2$ (10 mL) was added followed by water (10 mL). The aq. layer was extracted with $CH_2Cl_2$ (2×10 mL) and the combined org. extracts were dried over $MgSO_4$, filtered, and the solvents were removed under reduced pressure to give the title compound as a yellow oil. LC-MS-conditions 02: $t_R$=0.82 min; $[M+H+AcCN]^+$=270.24.

(E)-2-methyl-3-phenylacrylamide

In a flame dried round-bottomed flask equipped with a magnetic stir bar and under inert atmosphere ($N_2$), a solution of (E)-2-methyl-3-phenylacrylic acid (19.0 g, 116 mmol) and $Et_3N$ (17.1 mL, 122 mmol) in THF (500 mL) at 0° C. was treated with ethyl chloroformate (11.4 mL, 117 mmol) and the reaction mixture was stirred at 0° C. for 15 min. A solution of $NH_4OH$ (250 mL of a 25% aq. solution) in THF (150 mL) was then added and the reaction mixture was stirred at rt for 90 min. The aq. layer was extracted twice with $CH_2Cl_2$ and the combined org. extracts were washed with water, dried over $MgSO_4$, filtered, and the solvents were removed under reduced pressure to give the title compound as a white solid. TLC:rf (1000:50:4 $CH_2Cl_2$—MeOH—$NH_4OH$)=0.25

(E)-ethyl 2-(1-phenylprop-1-en-2-yl)oxazole-4-carboxylate

In a flame dried round-bottomed flask equipped with a magnetic stir bar and under inert atmosphere ($N_2$), a suspension of (E)-2-methyl-3-phenylacrylamide (29.4 g, 182 mmol) and $NaHCO_3$ (68.72 g, 820 mmol) in THF (500 mL) was treated with 3-bromo-2-oxo-propionic acid ethyl ester (45.74 mL, 309 mmol) and the reaction mixture was heated at reflux for 20 h. 3-Bromo-2-oxo-propionic acid ethyl ester (10.0 mL, 68 mmol) was added again and the reaction mixture was stirred at reflux for 10 h. The reaction mixture was then filtered over celite and the solvents were evaporated under reduced pressure. The residue was dissolved in THF (500 mL) and treated at 0° C., dropwise, with trifluoroacetic anhydride (78.0 mL, 555 mmol). The reaction mixture was then stirred at rt overnight. Sat. aq. $Na_2CO_3$ (250 mL) was added and the mixture was extracted with EA (4×250 mL), dried over $MgSO_4$, filtered, and the solvent was removed under reduced pressure. Purification of the residue by FC (0:1→1:9 EA-Hept) gave the title compound as a brown oil. TLC:rf (1:9 EA-Hept)=0.13.

Ethyl 2-acetyloxazole-4-carboxylate

In a flame dried round-bottomed flask equipped with a magnetic stir bar and under inert atmosphere ($N_2$), a solution of $NaIO_4$ (23 g, 108 mmol) in water (150) mL was slowly added to a vigorously stirred suspension of silica gel (110 g) in acetone (500 mL). The mixture was then concentrated under reduced pressure and the lumpy solid slurried in $CH_2Cl_2$ and the solvent was evaporated under reduced pressure. $CH_2Cl_2$ (500 mL) was added and the reaction mixture was treated at rt with (E)-ethyl 2-(1-phenylprop-1-en-2-yl)oxazole-4-carboxylate (8.3 g, 32.5 mmol) and $RuC_{1-3}$ hydrate (550 mg, 1.0 mmol). The reaction mixture was stirred at rt in the dark for 60 min, filtered and concentrated under reduced pressure. Purification of the residue by FC (1:0→1:5 petroleum ether: $Et_2O$) gave the title compound as a yellow solid. TLC:rf (1:1 EA-Hept)=0.52.

Ethyl 2-(1,1-Difluoroethyl)oxazole-4-carboxylate

In a flame dried round-bottomed flask equipped with a magnetic stir bar and under inert atmosphere ($N_2$), ethyl 2-acetyloxazole-4-carboxylate (1.15 g, 6.28 mmol) was treated with bis(2-methoxyethyl)aminosulfur trifluoride (7.31 g, 31.39 mmol) followed by EtOH (0.2 mL). The reaction mixture was stirred at 60° C. overnight. The reaction mixture was poured on sat. aq. $Na_2CO_3$ (25 mL). The aq. layer was extracted twice with EA and the combined org. extracts were washed with sat. aq. $Na_2CO_3$ (25 mL), water (25 mL) dried over $MgSO_4$, filtered, and the solvents were removed under reduced pressure. Purification of the residue by FC (5:1→1:1 hept-EA) gave the title compound as a yellow solid: TLC:rf (1:2 hept-EA)=0.8. LC-MS-conditions 01: $t_R$=0.85 min; $[M+H]^+$=205.98.

(2-(1,1-difluoroethyl)oxazol-4-yl)methanol

In a flame dried round-bottomed flask equipped with a magnetic stir bar and under inert atmosphere ($N_2$), a solution of ethyl 2-(1,1-difluoroethyl)oxazole-4-carboxylate (1.23 g, 6.00 mmol) in THF (15.0 mL) was added dropwise at 0° C. to a solution of lithim aluminium hydride (6.7 mL of a 1M sol in THF, 6.70 mmol) in THF (5.0 mL) and the reaction mixture was stirred for 1 h at 0° C. Water (2.0 mL) was added followed by 1M NaOH (2.0 mL) and water (2.0 mL) and the reaction mixture was allowed to warm to rt. The solvents were removed under reduced pressure to give the title compound as a colorless oil. TLC: rf (EA)=0.18. LC-MS-conditions 01: $t_R$=0.57 min; $[M+H]^+$=164.04.

2-(1,1-Difluoroethyl)-4-((4-nitro-2H-1,2,3-triazol-2-yl)methyl)oxazole

In a flame dried round-bottomed flask equipped with a magnetic stir bar and under inert atmosphere ($N_2$), a solution of (2-(1,1-difluoroethyl)oxazol-4-yl)methanol (505 mg, 3.10 mmol) in dry $CH_2Cl_2$ (15 mL) was treated at 0° C. with $Et_3N$ (0.56 mL, 4.03 mmol) followed by DMAP (38 mg, 0.31 mmol) and Ms-Cl (0.31 mL, 3.91 mmol). After stirring at 0° C. for 1.5 h, the reaction was quenched with water. The layers were separated and the aq. layer extracted with $CH_2Cl_2$ (3×) The org. layer was dried over $Na_2SO_4$, filtered, and the solvents were removed under reduced pressure to give 695 mg of crude (2-(1,1-difluoroethyl)oxazol-4-yl)methyl methanesulfonate as a yellow solid. A solution of this crude material in DMF (8 mL) was added to a solution of 4-nitro-2H-[1,2,3]triazole (3.08 g of a 10% solution in acetone, 2.70 mmol) in DMF (10 mL) pre-treated for 30 min with DIPEA (0.9 mL, 5.39 mmol) and the reaction mixture was stirred overnight at 50° C. Water (30 mL), followed by EA (50 mL) were added. The aq. layer was extracted with EA (50 mL) and the combined org. extracts were dried over $Na_2SO_4$, filtered, and the solvents were removed under reduced pressure. Purification of the residue by FC (5:1→2:1 hept-EA) gave the title compound as a yellow solid: TLC:rf (1:2 hept-EA)=0.4. LC-MS-conditions 01: $t_R$=0.89 min, $[M]^+$=259.11.

2-((2-(1,1-Difluoroethyl)oxazol-4-yl)methyl)-2H-1,2,3-triazol-4-amine

In a flame dried round-bottomed flask equipped with a magnetic stir bar and under inert atmosphere ($N_2$), a mixture of 2-(1,1-difluoroethyl)-4-(4-nitro-2H-1,2,3-triazol-2-yl) methyl)oxazole (130 mg, 0.50 mmol), iron powder (85 mg, 1.51 mmol) and $NH_4Cl$ (136 mg, 2.51 mmol) in a mixture of EtOH (2.0 mL) and water (1.0 mL) was stirred at 70° C. for 60 min. The reaction mixture was filtered while hot and concentrated under reduced pressure. $CH_2Cl_2$ (10 mL) was added followed by 1N NaOH (10 mL). The aq. layer was extracted with $CH_2Cl_2$ (2×10 mL) and the combined org. extracts were dried over $MgSO_4$, filtered, and the solvents were removed under reduced pressure to give the title compound as a yellow oil. LC-MS-conditions 01: $t_R$=0.66 min; $[M+H]^+$=230.03.

1-(2-((4-Nitro-2H-1,2,3-triazol-2-yl)methyl)thiazol-4-yl)ethanone

In a flame dried round-bottomed flask equipped with a magnetic stir bar and under inert atmosphere ($N_2$), a solution of 4-(2-methyl-1,3-dioxolan-2-yl)-2-(4-nitro-2H-1,2,3-triazol-2-yl)methyl)thiazole (WO2009077990A1) (5610 mg, 18.87 mmol) in THF (190 mL) was treated with 1N HCl (51.0 mL) and the reaction mixture was stirred overnight at rt. 1N NaOH was added to reach a neutral pH and the product was extracted with EA (2×100 mL). The combined org. extracts were dried over $MgSO_4$, filtered, and the solvents were removed under reduced pressure. Purification of the residue by FC (6:4 hept-EA) gave the title compound as a yellow solid: TLC:rf (6:4 hept-EA)=0.29. LC-MS-conditions 02: $t_R$=0.82 min.

1-(2-((4-Amino-2H-1,2,3-triazol-2-yl)methyl)thiazol-4-yl)ethanone

In a flame dried round-bottomed flask equipped with a magnetic stir bar and under inert atmosphere ($N_2$), a mixture of 1-(2-((4-nitro-2H-1,2,3-triazol-2-yl)methyl)thiazol-4-yl) ethanone (343 mg, 1.35 mmol), iron powder (229 mg, 4.06 mmol) and $NH_4Cl$ (366 mg, 6.77 mmol) in a mixture of EtOH (6.0 mL) and water (3.0 mL) was stirred at 85° C. for 20 min. The reaction mixture was filtered while hot and concentrated under reduced pressure. $CH_2Cl_2$ (20 mL) was added followed by water (20 mL). The aq. layer was extracted with $CH_2Cl_2$ (2×20 mL) and the combined org. extracts were dried over $MgSO_4$, filtered, and the solvents were removed under reduced pressure to give the title compound as a yellow oil. LC-MS-conditions 02: $t_R$=0.62 min; $[M+H]^+$=224.36.

1-(5-((4-Amino-2H-1,2,3-triazol-2-yl)methyl)furan-2-yl)ethanone

In a flame dried round-bottomed flask equipped with a magnetic stir bar and under inert atmosphere ($N_2$), a mixture of 1-(5-((4-nitro-2H-1,2,3-triazol-2-yl)methyl)furan-2-yl) ethanone (WO2009077990A1) (500 mg, 2.12 mmol), iron powder (358 mg, 6.35 mmol) and $NH_4Cl$ (572 mg, 10.59 mmol) in a mixture of EtOH (8.0 mL) and water (4.0 mL) was stirred at 85° C. for 30 min. The reaction mixture was filtered while hot and concentrated under reduced pressure. $CH_2Cl_2$ (15 mL) was added followed by 1N NaOH (15 mL). The aq. layer was extracted with $CH_2Cl_2$ (2×15 mL) and the combined org. extracts were dried over $MgSO_4$, filtered, and the solvents were removed under reduced pressure to give the title compound as a yellow oil. LC-MS-conditions 02: $t_R$=0.64 min; $[M+H]^+$=207.49.

N-(2-((4-(1,1-Difluoroethyl)oxazol-2-yl)methyl)-2H-1,2,3-triazol-4-yl)-5-(4-iodo-3-methylphenyl)-2-methyloxazole-4-carboxamide Following general procedure A, starting from 2-((4-(1,1-difluoroethyl)oxazol-2-yl)methyl)-2H-1,2,3-triazol-4-amine and 5-(4-iodo-3-methylphenyl)-2-methyloxazole-4-carboxylic acid. LC-MS-conditions 07: $t_R$=1.03 min; $[M+H]^+$=555.03.

N-(2-((4-(1,1-Difluoroethyl)oxazol-2-yl)methyl)-2H-1,2,3-triazol-4-yl)-5-(4-tritium-3-methylphenyl)-2-methyloxazole-4-carboxamide In a flame dried round-bottomed flask equipped with a magnetic stir bar and under inert atmosphere (N2), a suspension of N-(2-((4-(1,1-difluoroethyl)oxazol-2-yl)methyl)-2H-1,2,3-triazol-4-yl)-5-(4-iodo-3-methylphenyl)-2-methyloxazole-4-carboxamide (6.0 mg, 10.8 μmol), $Et_3N$ (3.0 μl, 22 μmol) and Pd (2.35 mg, 10% on charcoal) in DMF (0.6 mL) was degassed three times and stirred under an atmosphere of tritium gas (11 Ci) at 23° C. for 6 h. The solvent was removed under reduced pressure, and labile tritium was exchanged by adding 0.7 mL of MeOH, stirring the solution, and removing the solvent under reduced pressure. This process was repeated three times. Finally, the well dried solid was extracted with EtOH (10 mL) and the suspension was filtered through a 0.2 μm nylon membrane, obtaining a yellow solution. The activity of the crude product was 261 mCi. The RCP was determined to 93% using the following HPLC system: Macherey+Nagel Nucleodur C18 Gravity (5 μm, 4.6×150 mm); solvents: A. Water, 0.05% TFA; B: acetonitrile, 0.05% TFA; 0-4.5 min 65% B; 5-9.5 min 95% B; 10 min 65% B; 254 nM; flow 1.4 mL/min.

74 mCi of the crude product was purified using the following HPLC conditions: Macherey+Nagel Nucleodur C18 Gravity (5 μm, 8×150 mm); solvents: A: water, 0.1% TFA; B: acetonitrile, 0.1% TFA; 0-5.5 min 65% B; 6-9.5 min 95% B; 10 min 65% B; 254 nm, flow 4.0 ml/min.

The product fraction was diluted with water and $NaHCO_3$ was added before it was loaded on a SPE cartridge (Phenomenex StrataX, 3 mL, 100 mg), which was washed twice with water and eluted with EtOH (10 mL). The product showed a radiochemical purity of >97% and a specific activity of 23 Ci/mmol.

N-(2-((4-Acetylthiazol-2-yl)methyl)-2H-1,2,3-triazol-4-yl)-5-(4-iodo-3-methylphenyl)-2-methyloxazole-4-carboxamide Following general procedure A, starting from 1-(2-((4-amino-2H-1,2,3-triazol-2-yl)methyl)thiazol-4-yl)ethanone and 5-(4-iodo-3-methylphenyl)-2-methyloxazole-4-carboxylic acid. LC-MS-conditions 02: $t_R$=1.12 min; $[M+H]^+$=549.20.

N-(2-((4-Acetylthiazol-2-yl)methyl)-2H-1,2,3-triazol-4-yl)-5-(4-tritium-3-methylphenyl)-2-methyloxazole-4-carboxamide In a flame dried round-bottomed flask equipped with a magnetic stir bar and under inert atmosphere (N2), a suspension of N-(2-((4-acetylthiazol-2-yl)methyl)-2H-1,2,3-triazol-4-yl)-5-(4-iodo-3-methylphenyl)-2-methyloxazole-4-carboxamide (3.2 mg, 5.8 µmol), Et$_3$N (1.6 µl, 11.6 µmol) and Pd (1.55 mg, 10% on charcoal) in EtOH (0.46 mL) and dioxane (0.24 mL) was degassed three times and stirred under an atmosphere of tritium gas (12 Ci) at 21° C. for 5.5 h. The solvent was removed under reduced pressure, and labile tritium was exchanged by adding 1.0 mL of MeOH, stirring the solution, and removing the solvent under reduced pressure. This process was repeated three times. Finally, the well dried solid was extracted with EtOH (5 mL) and the suspension was filtered through a 0.2 µm nylon membrane, obtaining a colourless solution. The activity of the crude product was 111 mCi. The RCP was determined to 90% using the following HPLC system: Macherey+Nagel Nucleodur C8 Gravity (5 µm, 4.6×150 mm); solvents: A. Water, 0.05% TFA; B: acetonitrile, 0.05% TFA; 0 min 30% B; 10-14.5 min 95% B; 15 min 30% B; 290 nM; flow 1.0 mL/min.

60 mCi of the crude product was purified using the following HPCL conditions: Macherey+Nagel Nucleodur C18 Gravity (5 µm, 8×150 mm); solvents: A: water, 0.1% TFA; B: acetonitrile, 0.1% TFA; 53% B; 254 nm, flow 3.1 ml/min.

The product fraction was concentrated, NaHCO$_3$ was added before it was loaded on a SPE cartridge (Phenomenex StrataX, 3 mL, 100 mg), which was washed twice with water and eluted with EtOH. The product showed a radiochemical purity of >98% and a specific activity of 19 Ci/mmol.

N-(2-((5-Acetylfuran-2-yl)methyl)-2H-1,2,3-triazol-4-yl)-5-(4-iodo-3-methylphenyl)-2-methyloxazole-4-carboxamide Following general procedure A, starting from 1-(5-((4-amino-2H-1,2,3-triazol-2-yl)methyl)furan-2-yl)ethanone and 5-(4-iodo-3-methylphenyl)-2-methyloxazole-4-carboxylic acid. LC-MS-conditions 02: t$_R$=1.12 min; [M+H]$^+$=549.20.

N-(2-((5-Acetylfuran-2-yl)methyl)-2H-1,2,3-triazol-4-yl)-5-(4-tritium-3-methylphenyl)-2-methyloxazole-4-carboxamide In a flame dried round-bottomed flask equipped with a magnetic stir bar and under inert atmosphere (N2), a suspension of N-(2-((5-acetylfuran-2-yl)methyl)-2H-1,2,3-triazol-4-yl)-5-(4-iodo-3-methylphenyl)-2-methyloxazole-4-carboxamide (3.0 mg, 5.6 µmol), DIPEA (0.05 mL) and Pd (10 mg, 10% on charcoal) in EtOH (3.0 mL) and DMF (1.0 mL) was degassed three times and stirred under an atmosphere of tritium gas (5 Ci) at rt for 2.0 h. The catalyst was removed by filtration and labile tritium was removed by repeated evaporation to dryness from EtOH. Purification using the following HPCL conditions: Hypersil BDS C18 (5 µm, 4.6×250 mm); solvents: A: water, 0.1% TFA; B: acetonitrile, 0.1% TFA; gradient 100% A→100% B over 30 min, flow 1.0 ml/min.

Methyl 3-(dimethylamino)-4-fluorobenzoate

In a flame dried round-bottomed flask equipped with a magnetic stir bar and under inert atmosphere (N$_2$), a mixture of methyl 3-amino-4-fluorobenzoate (1.55 g, 9.16 mmol), paraformaldehyde (8.25 g, 91.63 mmol) and NaBH$_3$CN (1.73 g, 27.49 mmol) was treated with acetic acid (90 mL) and the resulting mixture was stirred at rt for 4 h. Sat. aq. Na$_2$CO$_3$ was added to the reaction mixture and the pH was adjusted to 7-8. The mixture was extracted with CH$_2$Cl$_2$ (3×55 mL) and the combined org. extracts were dried over MgSO$_4$, filtered, and the solvents were removed under reduced pressure to give the title compound as an orange oil. LC-MS-conditions 05c with a Waters Atlantis T3, 5 µm, 4.6×30 mm column: t$_R$=0.76 min; [M+H]$^+$=198.38.

2-Methyl-5-m-tolyl-oxazole-4-carboxylic acid

Prepared starting from 3-oxo-3-m-tolyl-propionic acid ethyl ester following sequentially general procedure F, G and E. LC-MS-conditions 02: t$_R$=0.85 min; [M+H]$^+$=218.46.

5-(3-Chloro-phenyl)-2-methyl-oxazole-4-carboxylic acid

Prepared starting from 3-chloro-benzoic acid following sequentially general procedure K, F, G and E. LC-MS-conditions 02: t$_R$=0.87 min; [M+H]$^+$=238.06.

2-Methyl-5-phenyl-oxazole-4-carboxylic acid

Prepared starting from 3-oxo-3-phenyl-propionic acid ethyl ester following sequentially general procedure F, G and E. LC-MS-conditions 02: t$_R$=0.76 min; [M+H]$^+$=204.03.

2-Methyl-5-(3-trifluoromethyl-phenyl)-oxazole-4-carboxylic acid

Prepared starting from 3-trifluoromethyl-benzoic acid following sequentially general procedure K, F, G and E. LC-MS-conditions 02: t$_R$=0.91 min; [M+H]$^+$=272.05.

2-Methyl-5-(3-trifluoromethoxy-phenyl)-oxazole-4-carboxylic acid

Prepared starting from 3-trifluoromethoxy-benzoic acid following sequentially general procedure K, F, G and E. LC-MS-conditions 02: t$_R$=0.93 min; [M+H]$^+$=288.06.

5-(4-Fluoro-phenyl)-oxazole-4-carboxylic acid

Prepared starting from 4-fluoro-benzoic acid following sequentially general procedure K, J, I, H and E. LC-MS-conditions 02: t$_R$=0.80 min; [M+AcCN+H]$^+$=249.04.

5-m-Tolyl-oxazole-4-carboxylic acid

Prepared starting from 3-oxo-3-m-tolyl-propionic acid ethyl ester following sequentially general procedure J, I, H and E. LC-MS-conditions 02: t$_R$=0.83 min; [M+H]$^+$=204.17.

5-(3-Methoxy-phenyl)-oxazole-4-carboxylic acid

Prepared starting from 3-(3-methoxy-phenyl)-3-oxo-propionic acid ethyl ester following sequentially general procedure J, I, H and E. LC-MS-conditions 02: t$_R$=0.80 min; [M+H]$^+$=220.13.

2-Ethyl-5-phenyl-oxazole-4-carboxylic acid

Prepared starting from 3-oxo-3-phenyl-propionic acid ethyl ester following sequentially general procedure J, I, H and E. LC-MS-conditions 02: $t_R$=0.85 min; [M+H]$^+$=218.19.

2-Cyclopropyl-5-phenyl-oxazole-4-carboxylic acid

Prepared starting from 3-oxo-3-phenyl-propionic acid ethyl ester following sequentially general procedure J, I, H and E. LC-MS-conditions 02: $t_R$=0.87 min; [M+H]$^+$=230.17.

5-(3-Fluoro-phenyl)-oxazole-4-carboxylic acid

Prepared starting from 3-fluoro-benzoic acid following sequentially general procedure K, J, I, H and E. LC-MS-conditions 02: $t_R$=0.80 min; [M+AcCN+H]$^+$=249.09.

5-(3-Chloro-phenyl)-oxazole-4-carboxylic acid

Prepared starting from 3-chloro-benzoic acid following sequentially general procedure K, J, I, H and E. LC-MS-conditions 02: $t_R$=0.85 min; [M+AcCN+H]$^+$=265.23.

5-(3-Dimethylamino-phenyl)-oxazole-4-carboxylic acid

Prepared starting from 3-dimethylamino-benzoic acid following sequentially general procedure M and E. LC-MS-conditions 02: $t_R$=0.60 min; [M+H]$^+$=233.36.

5-(3-Fluoro-5-methyl-phenyl)-2-methyl-oxazole-4-carboxylic acid

Prepared starting from 3-fluoro-5-methylbenzoic acid following sequentially general procedure N, O, P and E. LC-MS-conditions 02: $t_R$=0.88 min; [M+H]$^+$=277.28.

5-(3,5-Difluoro-phenyl)-2-methyl-oxazole-4-carboxylic acid

Prepared starting from 3,5-difluoro-benzoic acid following sequentially general procedure N, O, P and E. LC-MS-conditions 02: $t_R$=0.86 min; [M+AcCN+H]$^+$=281.19.

5-(4-Iodo-3-methylphenyl)-2-methyloxazole-4-carboxylic acid

Prepared starting from 4-iodo-3-methylbenzoic acid following sequentially general procedures K, Q, G and E. LC-MS-conditions 02: $t_R$=0.94 min; [M+H]$^+$=344.24.

5-(3-(Dimethylamino)-4-fluorophenyl)oxazole-4-carboxylic acid

Prepared starting from methyl 3-(dimethylamino)-4-fluorobenzoate following sequentially general procedures E, M and E. LC-MS-conditions 02: $t_R$=0.94 min; [M+H]$^+$=344.24.

5-(3-(Dimethylamino)-4-fluorophenyl)-2-methyloxazole-4-carboxylic acid

Prepared starting from methyl 3-(dimethylamino)-4-fluorobenzoate following sequentially general procedures E, M, O, H, E. LC-MS-conditions 05c with a Waters Atlantis T3, 5 μm, 4.6×30 mm column: $t_R$=0.59 min; [M+H]$^+$=265.25.

PREPARATION OF EXAMPLES

Example 1

2-Methyl-5-m-tolyl-oxazole-4-carboxylic acid {2-[5-(1,1-difluoro-ethyl)-furan-2-ylmethyl]-2H-[1,2,3]triazol-4-yl}-amide Following general procedure A, starting from 2-[5-(1,1-difluoro-ethyl)-furan-2-ylmethyl]-2H-[1,2,3]triazol-4-ylamine and 2-methyl-5-m-tolyl-oxazole-4-carboxylic acid. LC-MS-conditions 02: $t_R$=1.12 min; [M+H]$^+$=427.83.

Example 2

5-Phenyl-oxazole-4-carboxylic acid {2-[4-(1,1-difluoro-ethyl)-thiazol-2-ylmethyl]-2H-[1,2,3]triazol-4-yl}-amide Following general procedure A, starting from 2-[4-(1,1-Difluoro-ethyl)-thiazol-2-ylmethyl]-2H-[1,2,3]triazol-4-ylamine and 5-phenyl-oxazole-4-carboxylic acid. LC-MS-conditions 01: $t_R$=1.01 min; [M+H]$^+$=416.90.

Example 3

2-Methyl-5-m-tolyl-oxazole-4-carboxylic acid{2-[4-(1,1-difluoro-ethyl)-thiazol-2-ylmethyl]-2H-[1,2,3]triazol-4-yl}-amide Following general procedure A, starting from 2-[4-(1,1-Difluoro-ethyl)-thiazol-2-ylmethyl]-2H-[1,2,3]triazol-4-ylamine and 2-methyl-5-m-tolyl-oxazole-4-carboxylic acid. LC-MS-conditions 02: $t_R$=1.10 min; [M+H]$^+$=445.09.

Example 4

2-Methyl-5-phenyl-oxazole-4-carboxylic acid{2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 2-methyl-5-phenyl-oxazole-4-carboxylic acid. LC-MS-conditions 06: $t_R$=1.08 min; [M+H]$^+$=413.79.

Example 5

5-(3,5-Difluoro-phenyl)-2-methyl-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3,5-difluoro-phenyl)-2-methyl-oxazole-4-carboxylic acid. LC-MS-conditions 06: $t_R$=1.62 min; [M+H]$^+$=466.70.

Example 6

2-Methyl-5-(3-trifluoromethyl-phenyl)-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 2-methyl-5-(3-trifluoromethyl-phenyl)-oxazole-4-carboxylic acid. LC-MS-conditions 06: $t_R$=1.68 min; [M+H]$^+$=498.74.

Example 7

5-(3-Chloro-phenyl)-oxazole-4-carboxylic acid{2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-chloro-phenyl)-oxazole-4-carboxylic acid.
LC-MS-conditions 06: $t_R$=1.58 min; [M+H]$^+$=433.72.

Example 8

5-(3-Methoxy-phenyl)-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-methoxy-phenyl)-oxazole-4-carboxylic acid.
LC-MS-conditions 06: $t_R$=1.40 min; [M+H]$^+$=446.75.

Example 9

2-Cyclopropyl-5-phenyl-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 2-cyclopropyl-5-phenyl-oxazole-4-carboxylic acid.
LC-MS-conditions 06: $t_R$=1.68 min; [M+H]$^+$=456.74.

Example 10

2-Methyl-5-phenyl-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 2-methyl-5-phenyl-oxazole-4-carboxylic acid.
LC-MS-conditions 06: $t_R$=1.49 min; [M+H]$^+$=430.72.

Example 11

5-(3-Fluoro-phenyl)-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-fluoro-phenyl)-oxazole-4-carboxylic acid.
LC-MS-conditions 06: $t_R$=1.48 min; [M+H]$^+$=417.76.

Example 12

5-(3-Chloro-phenyl)-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-chloro-phenyl)-oxazole-4-carboxylic acid.
LC-MS-conditions 06: $t_R$=1.53 min; [M+H]$^+$=450.67.

Example 13

5-(3-Fluoro-5-methyl-phenyl)-2-methyl-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-fluoro-5-methyl-phenyl)-2-methyl-oxazole-4-carboxylic acid.
LC-MS-conditions 06: $t_R$=1.65 min; [M+H]$^+$=462.74.

Example 14

2-Methyl-5-(3-trifluoromethoxy-phenyl)-oxazole-4-carboxylic acid{2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 2-methyl-5-(3-trifluoromethoxy-phenyl)-oxazole-4-carboxylic acid.
LC-MS-conditions 06: $t_R$=1.72 min; [M+H]$^+$=514.74.

Example 15

5-(3-Chloro-phenyl)-2-methyl-oxazole-4-carboxylic acid{2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-chloro-phenyl)-2-methyl-oxazole-4-carboxylic acid.
LC-MS-conditions 06: $t_R$=1.70 min; [M+H]$^+$=447.75.

Example 16

5-(4-Fluoro-phenyl)-oxazole-4-carboxylic acid{2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(4-fluoro-phenyl)-oxazole-4-carboxylic acid.
LC-MS-conditions 06: $t_R$=1.47 min; [M+H]$^+$=417.76.

Example 17

5-m-Tolyl-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-m-tolyl-oxazole-4-carboxylic acid.
LC-MS-conditions 06: $t_R$=1.49 min; [M+H]$^+$=430.73.

Example 18

5-(3,5-Difluoro-phenyl)-2-methyl-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3,5-difluoro-phenyl)-2-methyl-oxazole-4-carboxylic acid.
LC-MS-conditions 06: $t_R$=1.66 min; [M+H]$^+$=449.74.

Example 19

5-(3-Dimethylamino-phenyl)-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-dimethylamino-phenyl)-oxazole-4-carboxylic acid.
LC-MS-conditions 06: $t_R$=1.55 min; [M+H]$^+$=442.5.

Example 20

5-(3-Fluoro-phenyl)-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-fluoro-phenyl)-oxazole-4-carboxylic acid.
LC-MS-conditions 06: $t_R$=1.42 min; [M+H]$^+$=434.74.

Example 21

5-(3-Methoxy-phenyl)-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-methoxy-phenyl)-oxazole-4-carboxylic acid.
LC-MS-conditions 06: $t_R$=1.46 min; [M+H]$^+$=429.79.

Example 22

5-(3-Dimethylamino-phenyl)-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-dimethylamino-phenyl)-oxazole-4-carboxylic acid.
LC-MS-conditions 06: $t_R$=1.50 min; [M+H]$^+$=459.89.

Example 23

5-m-Tolyl-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-m-tolyl-oxazole-4-carboxylic acid.
LC-MS-conditions 06: $t_R$=1.54 min; [M+H]$^+$=413.79.

Example 24

2-Methyl-5-(3-trifluoromethyl-phenyl)-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 2-methyl-5-(3-trifluoromethyl-phenyl)-oxazole-4-carboxylic acid.
LC-MS-conditions 06: $t_R$=1.72 min; [M+H]$^+$=481.8.

Example 25

5-(4-Fluoro-phenyl)-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(4-fluoro-phenyl)-oxazole-4-carboxylic acid.
LC-MS-conditions 06: $t_R$=1.42 min; [M+H]$^+$=434.74.

Example 26

5-(3-Fluoro-5-methyl-phenyl)-2-methyl-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-(3-fluoro-5-methyl-phenyl)-2-methyl-oxazole-4-carboxylic acid.
LC-MS-conditions 06: $t_R$=1.70 min; [M+H]$^+$=445.79.

Example 27

2-Methyl-5-(3-trifluoromethoxy-phenyl)-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 2-methyl-5-(3-trifluoromethoxy-phenyl)-oxazole-4-carboxylic acid.
LC-MS-conditions 06: $t_R$=1.76 min; [M+H]$^+$=497.74.

Example 28

5-Phenyl-oxazole-4-carboxylic acid {2-[5-(1,1-difluoro-ethyl)-furan-2-ylmethyl]-2H-[1,2,3]triazol-4-yl}-amide Following general procedure Z2, starting from 2-[5-(1,1-difluoro-ethyl)-furan-2-ylmethyl]-2H-[1,2,3]triazol-4-ylamine and 5-phenyl-oxazole-4-carboxylic acid.
LC-MS-conditions 06: $t_R$=1.49 min; [M+H]$^+$=399.78.

Example 29

5-(3-Chloro-phenyl)-2-methyl-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 5-(3-chloro-phenyl)-2-methyl-oxazole-4-carboxylic acid.
LC-MS-conditions 06: $t_R$=1.71 min; [M+H]$^+$=464.70.

Example 30

2-Ethyl-5-phenyl-oxazole-4-carboxylic acid {2-[4-(1,1-difluoro-ethyl)-thiazol-2-ylmethyl]-2H-[1,2,3]triazol-4-yl}-amide Following general procedure Z2, starting from 2-[4-(1,1-difluoro-ethyl)-thiazol-2-ylmethyl]-2H-[1,2,3]triazol-4-ylamine and 2-ethyl-5-phenyl-oxazole-4-carboxylic acid.
LC-MS-conditions 06: $t_R$=1.69 min; [M+H]$^+$=444.72.

Example 31

2-Methyl-5-m-tolyl-oxazole-4-carboxylic acid {2-[4-(1,1-difluoro-ethyl)-oxazol-2-ylmethyl]-2H-[1,2,3]triazol-4-yl}-amide Following general procedure A, starting from 2-[4-(1,1-difluoro-ethyl)-oxazol-2-ylmethyl]-2H-[1,2,3]triazol-4-ylamine and 2-methyl-5-m-tolyl-oxazole-4-carboxylic acid.
LC-MS-conditions 01: $t_R$=1.05 min; [M+H]$^+$=429.06.

Example 32

N-(2-((2-(1,1-Difluoroethyl)oxazol-4-yl)methyl)-2H-1,2,3-triazol-4-yl)-2-methyl-5-(m-tolyl)oxazole-4-carboxamide Following general procedure A, starting from 2-((2-(1,1-difluoroethyl)oxazol-4-yl)methyl)-2H-1,2,3-triazol-4-amine and 2-methyl-5-m-tolyl-oxazole-4-carboxylic acid.
LC-MS-conditions 01: $t_R$=1.05 min; [M+H]$^+$=429.06.

Example 33

2-Methyl-5-phenyl-oxazole-4-carboxylic acid {2-[4-(1,1-difluoro-ethyl)-oxazol-2-ylmethyl]-2H-[1,2,3]triazol-4-yl}-amide Following general procedure A, starting from 2-[4-(1,1-difluoro-ethyl)-oxazol-2-ylmethyl]-2H-[1,2,3]triazol-4-ylamine and 2-methyl-5-phenyloxazole-4-carboxylic acid.
LC-MS-conditions 08: $t_R$=1.28 min; [M+H]$^+$=415.00.

Example 34

5-(3-Dimethylamino-phenyl)-oxazole-4-carboxylic acid {2-[4-(1,1-difluoro-ethyl)-oxazol-2-ylmethyl]-2H-[1,2,3]triazol-4-yl}-amide Following general procedure A, starting from 2-[4-(1,1-difluoro-ethyl)-oxazol-2-ylmethyl]-2H-[1,2,3]triazol-4-ylamine and 5-(3-(dimethylamino)phenyl)oxazole-4-carboxylic acid.
LC-MS-conditions 08: $t_R$=1.29 min; [M+H]$^+$=444.04.

Example 35

5-(3-Dimethylamino-4-fluoro-phenyl)-oxazole-4-carboxylic acid {2-[4-(1,1-difluoro-ethyl)-oxazol-2-ylmethyl]-2H-[1,2,3]triazol-4-yl}-amide Following general procedure A, starting from 2-[4-(1,1-difluoro-ethyl)-oxazol-2-ylmethyl]-2H-[1,2,3]triazol-4-ylamine and 5-(3-(dimethylamino)-4-fluorophenyl)oxazole-4-carboxylic acid.
LC-MS-conditions 05c with a Waters Atlantis T3, 5 μm, 4.6×30 mm column: $t_R$=0.91 min; [M+H]$^+$=462.14.

Example 36

5-(3-Dimethylamino-4-fluoro-phenyl)-2-methyl-oxazole-4-carboxylic acid{2-[4-(1,1-difluoro-ethyl)-oxazol-2-ylmethyl]-2H-[1,2,3]triazol-4-yl}-amide Following general procedure A, starting from 2-[4-(1,1-difluoro-ethyl)-oxazol-2-ylmethyl]-2H-[1,2,3]triazol-4-ylamine and 5-(3-(dimethylamino)-4-fluorophenyl)-2-methyloxazole-4-carboxylic acid.
LC-MS-conditions 05c with a Waters Atlantis T3, 5 μm, 4.6×30 mm column: $t_R$=0.95 min; [M+H]$^+$=476.18.

II. Biological Assays
In Vitro Assay

The ALX receptor agonistic activity of the compounds of formula (I) is determined in accordance with the following experimental method.
Experimental Method:
Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1'000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 μM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50'000 cells in 70 μl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor ($EC_{50}$ values) of exemplified compounds are displayed in Table 1.

TABLE 1

| Compound | $EC_{50}$ [nM] |
|---|---|
| Example 1: 2-Methyl-5-m-tolyl-oxazole-4-carboxylic acid {2-[5-(1,1-difluoro-ethyl)-furan-2-ylmethyl]-2H-[1,2,3]triazol-4-yl}-amide | 8.1 |
| Example 2: 5-Phenyl-oxazole-4-carboxylic acid {2-[4-(1,1-difluoro-ethyl)-thiazol-2-ylmethyl]-2H-[1,2,3]triazol-4-yl}-amide | 19 |
| Example 3: 2-Methyl-5-m-tolyl-oxazole-4-carboxylic acid {2-[4-(1,1-difluoro-ethyl)-thiazol-2-ylmethyl]-2H-[1,2,3]triazol-4-yl}-amide | 7.7 |

TABLE 1-continued

| Compound | EC$_{50}$ [nM] |
|---|---|
| Example 4:<br>2-Methyl-5-phenyl-oxazole-4-carboxylic acid {2-[5-(1,1-difluoro-ethyl)-furan-2-ylmethyl]-2H-[1,2,3]triazol-4-yl}-amide | 0.9 |
| Example 5:<br>5-(3,5-Difluoro-phenyl)-2-methyl-oxazole-4-carboxylic acid {2-[4-(1,1-difluoro-ethyl)-thiazol-2-ylmethyl]-2H-[1,2,3]triazol-4-yl}-amide | 818 |
| Example 6:<br>2-Methyl-5-(3-trifluoromethyl-phenyl)-oxazole-4-carboxylic acid {2-[4-(1,1-difluoro-ethyl)-thiazol-2-ylmethyl-2H-[1,2,3]triazol-4-yl}-amide | 14 |
| Example 7:<br>5-(3-Chloro-phenyl)-oxazole-4-carboxylic acid {2-[5-(1,1-difluoro-ethyl)-furan-2-ylmethyl]-2H-[1,2,3]triazol-4-yl}-amide | 17 |
| Example 8:<br>5-(3-Methoxy-phenyl)-oxazole-4-carboxylic acid {2-[4-(1,1-difluoro-ethyl)-thiazol-2-ylmethyl]-2H-[1,2,3]triazol-4-yl}-amide | 69 |
| Example 9:<br>2-Cyclopropyl-5-phenyl-oxazole-4-carboxylic acid {2-[4-(1,1-difluoro-ethyl)-thiazol-2-ylmethyl]-2H-[1,2,3]triazol-4-yl}-amide | 291 |
| Example 10:<br>2-Methyl-5-phenyl-oxazole-4-carboxylic acid {2-[4-(1,1-difluoro-ethyl)-thiazol-2-ylmethyl]-2H-[1,2,3]triazol-4-yl}-amide | 6.3 |
| Example 11:<br>5-(3-Fluoro-phenyl)-oxazole-4-carboxylic acid {2-[5-(1,1-difluoro-ethyl)-furan-2-ylmethyl]-2H-[1,2,3]triazol-4-yl}-amide | 9.9 |
| Example 12:<br>5-(3-Chloro-phenyl)-oxazole-4-carboxylic acid {2-[4-(1,1-difluoro-ethyl)-thiazol-2-ylmethyl]-2H-[1,2,3]triazol-4-yl}-amide | 46 |
| Example 13:<br>5-(3-Fluoro-5-methyl-phenyl)-2-methyl-oxazole-4-carboxylic acid {2-[4-(1,1-difluoro-ethyl)-thiazol-2-ylmethyl]-2H-[1,2,3]triazol-4-yl}-amide | 1130 |
| Example 14:<br>2-Methyl-5-(3-trifluoromethoxy-phenyl)-oxazole-4-carboxylic acid {2-[4-(1,1-difluoro-ethyl)-thiazol-2-ylmethyl]-2H-[1,2,3]triazol-4-yl}-amide | 58 |
| Example 15:<br>5-(3-Chloro-phenyl)-2-methyl-oxazole-4-carboxylic acid {2-[5-(1,1-difluoro-ethyl)-furan-2-ylmethyl]-2H-[1,2,3]triazol-4-yl}-amide | 23 |
| Example 16:<br>5-(4-Fluoro-phenyl)-oxazole-4-carboxylic acid {2-[5-(1,1-difluoro-ethyl)-furan-2-ylmethyl]-2H-[1,2,3]triazol-4-yl}-amide | 46 |
| Example 17:<br>5-m-Tolyl-oxazole-4-carboxylic acid {2-[4-(1,1-difluoro-ethyl)-thiazol-2-ylmethyl]-2H-[1,2,3]triazol-4-yl}-amide | 11 |
| Example 18:<br>5-(3,5-Difluoro-phenyl)-2-methyl-oxazole-4-carboxylic acid {2-[5-(1,1-difluoro-ethyl)-furan-2-ylmethyl]-2H-[1,2,3]triazol-4-yl}-amide | 661 |
| Example 19:<br>5-(3-Dimethylamino-phenyl)-oxazole-4-carboxylic acid {2-[5-(1,1-difluoro-ethyl)-furan-2-ylmethyl]-2H-[1,2,3]triazol-4-yl}-amide | 33 |
| Example 20:<br>5-(3-Fluoro-phenyl)-oxazole-4-carboxylic acid {2-[4-(1,1-difluoro-ethyl)-thiazol-2-ylmethyl]-2H-[1,2,3]triazol-4-yl}-amide | 55 |
| Example 21:<br>5-(3-Methoxy-phenyl)-oxazole-4-carboxylic acid {2-[5-(1,1-difluoro-ethyl)-furan-2-ylmethyl]-2H-[1,2,3]triazol-4-yl}-amide | 35 |
| Example 22:<br>5-(3-Dimethylamino-phenyl)-oxazole-4-carboxylic acid {2-[4-(1,1-difluoro-ethyl)-thiazol-2-ylmethyl]-2H-[1,2,3]triazol-4-yl}-amide | 52 |
| Example 23:<br>5-m-Tolyl-oxazole-4-carboxylic acid {2-[5-(1,1-difluoro-ethyl)-furan-2-ylmethyl]-2H-[1,2,3]triazol-4-yl}-amide | 10 |
| Example 24:<br>2-Methyl-5-(3-trifluoromethyl-phenyl)-oxazole-4-carboxylic acid {2-[5-(1,1-difluoro-ethyl)-furan-2-ylmethyl]-2H-[1,2,3]triazol-4-yl}-amide | 2.1 |
| Example 25:<br>5-(4-Fluoro-phenyl)-oxazole-4-carboxylic acid {2-[4-(1,1-difluoro-ethyl)-thiazol-2-ylmethyl]-2H-[1,2,3]triazol-4-yl}-amide | 221 |
| Example 26:<br>5-(3-Fluoro-5-methyl-phenyl)-2-methyl-oxazole-4-carboxylic acid {2-[5-(1,1-difluoro-ethyl)-furan-2-ylmethyl]-2H-[1,2,3]triazol-4-yl}-amide | 742 |
| Example 27:<br>2-Methyl-5-(3-trifluoromethoxy-phenyl)-oxazole-4-carboxylic acid {2-[5-(1,1-difluoro-ethyl)-furan-2-ylmethyl]-2H-[1,2,3]triazol-4-yl}-amide | 59 |
| Example 28:<br>5-Phenyl-oxazole-4-carboxylic acid {2-[5-(1,1-difluoro-ethyl)-furan-2-ylmethyl]-2H-[1,2,3]triazol-4-yl}-amide | 6.0 |

TABLE 1-continued

| Compound | EC$_{50}$ [nM] |
|---|---|
| Example 29:<br>5-(3-Chloro-phenyl)-2-methyl-oxazole-4-carboxylic acid {2-[4-(1,1-difluoro-ethyl)-thiazol-2-ylmethyl]-2H-[1,2,3]triazol-4-yl}-amide | 5.6 |
| Example 30:<br>2-Ethyl-5-phenyl-oxazole-4-carboxylic acid {2-[4-(1,1-difluoro-ethyl)-thiazol-2-ylmethyl]-2H-[1,2,3]triazol-4-yl}-amide | 11 |
| Example 31:<br>2-Methyl-5-m-tolyl-oxazole-4-carboxylic acid {2-[4-(1,1-difluoro-ethyl)-oxazol-2-ylmethyl]-2H-[1,2,3]triazol-4-yl}-amide | 2.4 |
| Example 32:<br>N-(2-((2-(1,1-Difluoroethyl)oxazol-4-yl)methyl)-2H-1,2,3-triazol-4-yl)-2-methyl-5-(m-tolyl)oxazole-4-carboxamide | 12 |
| Example 33:<br>2-Methyl-5-phenyl-oxazole-4-carboxylic acid {2-[4-(1,1-difluoro-ethyl)-oxazol-2-ylmethyl]-2H-[1,2,3]triazol-4-yl}-amide | 2.9 |
| Example 34:<br>5-(3-Dimethylamino-phenyl)-oxazole-4-carboxylic acid {2-[4-(1,1-difluoro-ethyl)-oxazol-2-ylmethyl]-2H-[1,2,3]triazol-4-yl}-amide | 6.1 |
| Example 35:<br>5-(3-Dimethylamino-4-fluoro-phenyl)-oxazole-4-carboxylic acid {2-[4-(1,1-difluoro-ethyl)-oxazol-2-ylmethyl]-2H-[1,2,3]triazol-4-yl}-amide | 4.0 |
| Example 36:<br>5-(3-Dimethylamino-4-fluoro-phenyl)-2-methyl-oxazole-4-carboxylic acid {2-[4-(1,1-difluoro-ethyl)-oxazol-2-ylmethyl]-2H-[1,2,3]triazol-4-yl}-amide | 77 |

Assay for Covalent Binding Between Reactive Metabolites and Proteins Using Human Liver Microsomes The objective of the described covalent binding assay is to determine the amount of covalent binding between reactive metabolites and proteins of human liver microsomes (HLM) per hour following incubation in the presence of an NADPH regenerating system. The measured covalent binding rate is expressed in pmol bound drug equivalent/mg protein/h. It is a well-known advantage if compounds have a low tendency to bind covalently to proteins.

Incubation

The radiolabelled compounds ($^3$H or $^{14}$C) were incubated at a concentration of 10 μM in a single 96 well plate with 1.0 mg/mL of human liver microsomes in 0.1 M phosphate buffer (pH 7.4). To this end, a volume of 2.5 μL 1 mM stock solution prepared in the respective solvent (ethanol) was added to a final volume of 250 μL. Incubations were performed in the absence or presence of the NADPH-regenerating system with glucose-6-phosphate dehydrogenase (20 IU/ml dehydrogenase, 25 μl with 11 mM NADP sodium salt, 100 mM glucose-6-phosphate disodium salt, 100 mM MgCl$_2$ in 0.1 M Tris buffer, pH 7.4) and additionally in the absence or presence of 5 mM GSH to trap reactive intermediates. An initial blank value without NADPH without incubation was also determined to determine unspecific rapid binding. Reactions were initiated by addition of 25 μL of an NADPH-regenerating system and terminated after one hour by adding 200 μL of the incubation mixture on a multiscreen deep well solvinert 96 hydrophobic PTFE filter plate (Millipore, Zug, Switzerland) containing 260 μL of ice-cold acetonitrile. The precipitation of microsomal proteins was completed by shaking the plate at 600 rpm at a temperature of 15° C. for 15 min. Finally, the precipitated incubation was stored at 4° C. for 15 min in the fridge. Proteins and filtrates were separated by centrifugation at 1800 g for 20 min at 10° C. The protein pellet was washed to remove unspecific binding with 800 μL of methanol/0.1% sulfuric acid (v/v) by centrifugation at 1500 g, 10° C. and 2 min. The washing step was repeated six times. The washed protein pellet was redissolved by addition of 500 μL of aqueous 0.1% (w/v) NaOH/1% (w/v) SDS. The filter plate was shaken at 400 rpm for 45 min at 60° C. and centrifugated at 2000 g for 20 min at 35° C. This step was repeated once and the protein solutions were combined.

For the determination of total radioactivity, an aliquot of 400 μL protein solution was mixed with 4 mL of liquid scintillation cocktail (Irga Safe plus, Perkin Elmer, Zurich, Switzerland) and analyzed using a Tricarb 2300 TR liquid scintillation analyzer (Perkin Elmer) with luminescence correction and on-line quenching correction by means of an external standard ($^{133}$Ba). For the determination of total protein content, an aliquot of 20 μL protein solution was analyzed using the BCA protein assay kit (Perbio Science Switzerland SA, Lausanne, Switzerland). The amount of covalent binding to microsomal proteins was calculated as follows: Dividing the determined amount of bound drug equivalent with NADPH (background subtracted by the amount of bound drug equivalent without NADPH) by the calculated amount of protein of redissolved washed protein pellet in each well gives the amount of bound drug equivalent in pmol/mg protein per hour.

The following results demonstrate a superior covalent binding profile of example 31 of the present application compared to examples 18 and 75 of WO 2009/077990, indicating a lower risk for adverse side effects; the preparation of the tritiated compounds is described in the experimental part.

|  | Example 18 of WO 2009/077990 | Example 75 of WO 2009/077990 | Example 31 |
|---|---|---|---|
| HLM without NADPH | 53 | 6 | 3 |
| HLM with NADPH | 1975 | 270 | 22 |
| HLM with NADPH and GSH | 374 | 72 | 28 |
| HLM with NADPH (background corrected as described above) [amount of bound drug equivalent in pmol/mg protein per hour] | 1922 | 264 | 19 |

The invention claimed is:
1. A compound of the formula (I),

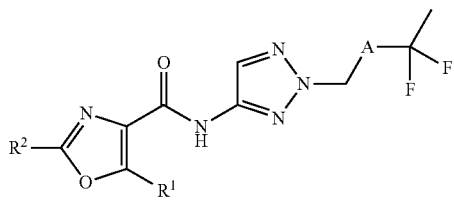

wherein
A represents a heteroaryl-group, wherein the two attachment-points of said heteroaryl-group are in a 1,3-arrangement;
R¹ represents phenyl which is unsubstituted, mono- or di-substituted, wherein the substituents independently is halogen, methyl, methoxy, trifluoromethyl, trifluoromethoxy or dimethylamino; and
R² represents hydrogen, methyl, ethyl or cyclopropyl;
or a pharmaceutically acceptable salt thereof.

2. The compound according to claim 1,
wherein
A represents a group selected from furanyl, oxazolyl or thiazolyl, wherein the two attachment-points of said group are in a 1,3-arrangement;
R¹ represents phenyl which is unsubstituted, mono- or di-substituted, wherein the substituents independently is fluoro, chloro, methyl, methoxy, trifluoromethyl, trifluoromethoxy or dimethylamino; and
R² represents hydrogen, methyl or ethyl;
or a pharmaceutically acceptable salt thereof.

3. The compound according to claim 2, wherein A represents furan-2,5-diyl, oxazol-2,4-diyl or thiazol-2,4-diyl; or a pharmaceutically acceptable salt thereof.

4. The compound according to claim 2, wherein A represents furan-2,5-diyl; or a pharmaceutically acceptable salt thereof.

5. The compound according to claim 2, wherein A represents oxazol-2,4-diyl; or a pharmaceutically acceptable salt thereof.

6. The compound according to claim 2, wherein A represents thiazol-2,4-diyl; or a pharmaceutically acceptable salt thereof.

7. The compound according to claim 2, wherein R¹ represents unsubstituted phenyl; or a pharmaceutically acceptable salt thereof.

8. The compound according to claim 2, wherein R¹ represents phenyl, which is mono-substituted with fluoro, chloro, methyl or trifluoromethyl; or a pharmaceutically acceptable salt thereof.

9. The compound according to claim 8, wherein R² represents hydrogen; or a pharmaceutically acceptable salt thereof.

10. The compound according to claim 8, wherein R² represents methyl or ethyl; or a pharmaceutically acceptable salt thereof.

11. The compound according to claim 1, selected from:
2-Methyl-5-m-tolyl-oxazole-4-carboxylic acid {2-[5-(1,1-difluoro-ethyl)-furan-2-ylmethyl]-2H-[1,2,3]triazol-4-yl}-amide;
5-Phenyl-oxazole-4-carboxylic acid {2-[4-(1,1-difluoro-ethyl)-thiazol-2-ylmethyl]-2H-[1,2,3]triazol-4-yl}-amide;
2-Methyl-5-m-tolyl-oxazole-4-carboxylic acid {2-[4-(1,1-difluoro-ethyl)-thiazol-2-ylmethyl]-2H-[1,2,3]triazol-4-yl}-amide;
2-Methyl-5-phenyl-oxazole-4-carboxylic acid {2-[5-(1,1-difluoro-ethyl)-furan-2-ylmethyl]-2H-[1,2,3]triazol-4-yl}-amide;
5-(3,5-Difluoro-phenyl)-2-methyl-oxazole-4-carboxylic acid {2-[4-(1,1-difluoro-ethyl)-thiazol-2-ylmethyl]-2H-[1,2,3]triazol-4-yl}-amide;
2-Methyl-5-(3-trifluoromethyl-phenyl)-oxazole-4-carboxylic acid {2-[4-(1,1-difluoro-ethyl)-thiazol-2-ylmethyl]-2H-[1,2,3]triazol-4-yl}-amide;
5-(3-Chloro-phenyl)-oxazole-4-carboxylic acid {2-[5-(1,1-difluoro-ethyl)-furan-2-ylmethyl]-2H-[1,2,3]triazol-4-yl}-amide;
5-(3-Methoxy-phenyl)-oxazole-4-carboxylic acid {2-[4-(1,1-difluoro-ethyl)-thiazol-2-ylmethyl]-2H-[1,2,3]triazol-4-yl}-amide;
2-Cyclopropyl-5-phenyl-oxazole-4-carboxylic acid {2-[4-(1,1-difluoro-ethyl)-thiazol-2-ylmethyl]-2H-[1,2,3]triazol-4-yl}-amide;
2-Methyl-5-phenyl-oxazole-4-carboxylic acid {2-[4-(1,1-difluoro-ethyl)-thiazol-2-ylmethyl]-2H-[1,2,3]triazol-4-yl}-amide;
5-(3-Fluoro-phenyl)-oxazole-4-carboxylic acid {2-[5-(1,1-difluoro-ethyl)-furan-2-ylmethyl]-2H-[1,2,3]triazol-4-yl}-amide;
5-(3-Chloro-phenyl)-oxazole-4-carboxylic acid {2-[4-(1,1-difluoro-ethyl)-thiazol-2-ylmethyl]-2H-[1,2,3]triazol-4-yl}-amide;
5-(3-Fluoro-5-methyl-phenyl)-2-methyl-oxazole-4-carboxylic acid {2-[4-(1,1-difluoro-ethyl)-thiazol-2-ylmethyl]-2H-[1,2,3]triazol-4-yl}-amide;
2-Methyl-5-(3-trifluoromethoxy-phenyl)-oxazole-4-carboxylic acid {2-[4-(1,1-difluoro-ethyl)-thiazol-2-ylmethyl]-2H-[1,2,3]triazol-4-yl}-amide;
5-(3-Chloro-phenyl)-2-methyl-oxazole-4-carboxylic acid {2-[5-(1,1-difluoro-ethyl)-furan-2-ylmethyl]-2H-[1,2,3]triazol-4-yl}-amide;
5-(4-Fluoro-phenyl)-oxazole-4-carboxylic acid {2-[5-(1,1-difluoro-ethyl)-furan-2-ylmethyl]-2H-[1,2,3]triazol-4-yl}-amide;
5-m-Tolyl-oxazole-4-carboxylic acid {2-[4(1,1-difluoro-ethyl)-thiazol-2-ylmethyl]-2H-[1,2,3]triazol-4-yl}-amide;
5-(3,5-Difluoro-phenyl)-2-methyl-oxazole-4-carboxylic acid {2-[5-(1,1-difluoro-ethyl)-furan-2-ylmethyl]-2H-[1,2,3]triazol-4-yl}-amide;
5-(3-Dimethylamino-phenyl)-oxazole-4-carboxylic acid {2-[5-(1,1-difluoro-ethyl)-furan-2-ylmethyl]-2H-[1,2,3]triazol-4-yl}-amide;
5-(3-Fluoro-phenyl)-oxazole-4-carboxylic acid {2-[4-(1,1-difluoro-ethyl)-thiazol-2-ylmethyl]-2H-[1,2,3]triazol-4-yl}-amide;
5-(3-Methoxy-phenyl)-oxazole-4-carboxylic acid {2-[5-(1,1-difluoro-ethyl)-furan-2-ylmethyl]-2H-[1,2,3]triazol-4-yl}-amide;
5-(3-Dimethylamino-phenyl)-oxazole-4-carboxylic acid {2-[4-(1,1-difluoro-ethyl)-thiazol-2-ylmethyl]-2H-[1,2,3]triazol-4-yl}amide;
5-m-Tolyl-oxazole-4-carboxylic acid {2-[5-(1,1-difluoro-ethyl)-furan-2-ylmethyl]-2H-[1,2,3]triazol-4-yl}-amide;
2-Methyl-5-(3-trifluoromethyl-phenyl)-oxazole-4-carboxylic acid {2-[5(1,1-difluoro-ethyl)-furan-2-ylmethyl]-2H-[1,2,3]triazol-4-yl}amide;

5-(4-Fluoro-phenyl)-oxazole-4-carboxylic acid {2-[4-(1,1-difluoro-ethyl)-thiazol-2-ylmethyl]-2H-[1,2,3]triazol-4-yl}-amide;

5-(3-Fluoro-5-methyl-phenyl)-2-methyl-oxazole-4-carboxylic acid {2-[5-(1,1-difluoro-ethyl)-furan-2-ylmethyl]-2H-[1,2,3]triazol-4-yl}amide;

2-Methyl-5-(3-trifluoromethoxy-phenyl)-oxazole-4-carboxylic acid {2-[5-(1,1-difluoro-ethyl)-furan-2-ylmethyl]-2H-[1,2,3]triazol-4-yl}-amide;

5-Phenyl-oxazole-4-carboxylic acid {2-[5-(1,1-difluoro-ethyl)-furan-2-ylmethyl]-2H-[1,2,3]triazol-4-yl}-amide;

5-(3-Chloro-phenyl)-2-methyl-oxazole-4-carboxylic acid {2-[4-(1,1-difluoro-ethyl)-thiazol-2-ylmethyl]-2H-[1,2,3]triazol-4-yl}-amide;

2-Ethyl-5-phenyl-oxazole-4-carboxylic acid {2-[4-(1,1-difluoro-ethyl)-thiazol-2-ylmethyl]-2H-[1,2,3]triazol-4-yl}amide; or 2-Methyl-5-m-tolyl-oxazole-4-carboxylic acid {2-[4(1,1-difluoro-ethyl)-oxazol-2-ylmethyl]-2H-[1,2,3]triazol-4-yl}-amide;

or a pharmaceutically acceptable salt thereof.

12. The compound according to claim 1, selected from:

N-(2-((2-(1,1-Difluoroethyl)oxazol-4-yl)methyl)-2H-1,2,3-triazol-4-yl)-2-methyl-5-(m-tolyl)oxazole-4-carboxamide;

2-Methyl-5-phenyl-oxazole-4-carboxylic acid {2-[4-(1,1-difluoro-ethyl)-oxazol-2-ylmethyl]-2H-[1,2,3]triazol-4-yl}-amide;

5-(3-Dimethylamino-phenyl)-oxazole-4-carboxylic acid {2-[4-(1,1-difluoro-ethyl)-oxazol-2-ylmethyl]-2H-[1,2,3]triazol-4-yl}-amide;

5-(3-Dimethylamino-4-fluoro-phenyl)-oxazole-4-carboxylic acid {2-[4-(1,1-difluoro-ethyl)-oxazol-2-ylmethyl]-2H-[1,2,3]triazol-4-yl}amide; or 5-(3-Dimethylamino-4-fluoro-phenyl)-2-methyl-oxazole-4-carboxylic acid {2-[4(1,1-difluoro-ethyl)-oxazol-2-ylmethyl]-2H-[1,2,3]triazol-4-yl}amide;

or a pharmaceutically acceptable salt thereof.

13. A pharmaceutical composition comprising a compound according to claim 1 or a pharmaceutically acceptable salt thereof, and at least one therapeutically inert excipient.

14. A method of treating a disease comprising administering to a subject in need thereof, a compound according to claim 1, or a pharmaceutically acceptable salt thereof, wherein the disease is selected from inflammatory diseases, obstructive airway diseases, allergic conditions, HIV-mediated retroviral infections, cardiovascular disorders, neuroinflammation, neurological disorders, pain, prion-mediated diseases or amyloid-mediated disorders; or for the modulation of immune responses.

15. A method of treating a disease comprising administering to a subject in need thereof, a composition according to claim 13, wherein the disease is selected from inflammatory diseases, obstructive airway diseases, allergic conditions, HIV-mediated retroviral infections, cardiovascular disorders, neuroinflammation, neurological disorders, pain, prion-mediated diseases or amyloid-mediated disorders; or for the modulation of immune responses.

16. The compound according to claim 5, wherein $R^1$ represents phenyl, which is mono-substituted with fluoro, chloro, methyl or trifluoromethyl; or a pharmaceutically acceptable salt thereof.

17. The compound according to claim 6, wherein $R^1$ represents phenyl, which is mono-substituted with fluoro, chloro, methyl or trifluoromethyl; or a pharmaceutically acceptable salt thereof.

18. The compound according to claim 1, wherein the compound is:
2-Methyl-5-phenyl-oxazole-4-carboxylic acid {2-[5-(1,1-difluoro-ethyl)-furan-2-ylmethyl]-2H-[1,2,3]triazol-4-yl}-amide; or a pharmaceutically acceptable salt thereof.

19. The compound according to claim 1, wherein the compound is:
2-Methyl-5-(3-trifluoromethyl-phenyl)-oxazole-4-carboxylic acid {2-[5-(1,1-difluoro-ethyl)-furan-2-ylmethyl]-2H-[1,2,3]triazol-4-yl}-amide; or a pharmaceutically acceptable salt thereof.

20. The compound according to claim 1, wherein the compound is:
2-Methyl-5-m-tolyl-oxazole-4-carboxylic acid {2-[4-(1,1-difluoro-ethyl)-oxazol-2-ylmethyl]-2H-[1,2,3]triazol-4-yl}-amide; or a pharmaceutically acceptable salt thereof.

21. The compound according to claim 1, wherein the compound is:
2-Methyl-5-phenyl-oxazole-4-carboxylic acid {2-[4-(1,1-difluoro-ethyl)-oxazol-2-ylmethyl]-2H-[1,2,3]triazol-4-yl}-amide; or a pharmaceutically acceptable salt thereof.

22. The compound according to claim 1, wherein the compound is:
5-(3-Chloro-phenyl)-2-methyl-oxazole-4-carboxylic acid {2-[4-(1,1-difluoro-ethyl)-thiazol-2-ylmethyl]-2H-[1,2,3]triazol-4-yl}-amide; or a pharmaceutically acceptable salt thereof.

* * * * *